US010640452B2

(12) United States Patent
Clendennen et al.

(10) Patent No.: US 10,640,452 B2
(45) Date of Patent: May 5, 2020

(54) BRANCHED TRIALKYL QUATERNARY AMMONIUM COMPOUNDS

(71) Applicant: Eastman Chemical Company, Kingsport, TN (US)

(72) Inventors: Stephanie Kay Clendennen, Kingsport, TN (US); Vasudev R. Bhonde, Johnson City, TN (US); Damon Ray Billodeaux, Longview, TX (US); Matthew Allen Boone, Kingsport, TN (US); Kim Dumoleijn, Eede (NL); Stijn Simonne Paul Van de Vyver, Ghent (BE); Kristof Moonen, Hamme (BE); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/243,237

(22) Filed: Jan. 9, 2019

(65) Prior Publication Data
US 2019/0218171 A1    Jul. 18, 2019

Related U.S. Application Data

(60) Provisional application No. 62/616,502, filed on Jan. 12, 2018.

(51) Int. Cl.
| C07C 207/02 | (2006.01) |
| C07C 201/00 | (2006.01) |
| C11D 1/75 | (2006.01) |
| C11D 1/83 | (2006.01) |
| C11D 1/835 | (2006.01) |
| C11D 1/94 | (2006.01) |
| C10L 1/18 | (2006.01) |
| C11D 3/39 | (2006.01) |
| C11D 11/00 | (2006.01) |
| C11D 3/43 | (2006.01) |
| C09D 7/63 | (2018.01) |
| C09K 8/584 | (2006.01) |
| C11D 3/395 | (2006.01) |
| A01N 41/08 | (2006.01) |
| C07C 311/32 | (2006.01) |
| C07C 211/08 | (2006.01) |
| C09K 8/524 | (2006.01) |
| A01N 37/44 | (2006.01) |
| C07C 291/04 | (2006.01) |
| C07C 45/74 | (2006.01) |
| C07C 215/10 | (2006.01) |
| C07C 45/62 | (2006.01) |
| A61K 8/41 | (2006.01) |
| A61K 8/44 | (2006.01) |
| A61K 8/46 | (2006.01) |
| A61Q 5/02 | (2006.01) |

(Continued)

(52) U.S. Cl.
CPC .......... *C07C 207/02* (2013.01); *A01N 33/12* (2013.01); *A01N 37/44* (2013.01); *A01N 41/08* (2013.01); *A61K 8/416* (2013.01); *A61K 8/44* (2013.01); *A61K 8/466* (2013.01); *A61Q 5/02* (2013.01); *A61Q 19/10* (2013.01); *B01J 31/0239* (2013.01); *C07C 45/62* (2013.01); *C07C 45/72* (2013.01); *C07C 45/74* (2013.01); *C07C 201/00* (2013.01); *C07C 209/22* (2013.01); *C07C 211/04* (2013.01); *C07C 211/08* (2013.01); *C07C 211/63* (2013.01); *C07C 211/64* (2013.01); *C07C 215/10* (2013.01); *C07C 229/12* (2013.01); *C07C 291/04* (2013.01); *C07C 309/14* (2013.01); *C07C 311/32* (2013.01); *C07H 5/06* (2013.01); *C09D 7/63* (2018.01); *C09K 8/524* (2013.01); *C09K 8/584* (2013.01); *C10L 1/18* (2013.01); *C11D 1/75* (2013.01); *C11D 1/83* (2013.01); *C11D 1/835* (2013.01); *C11D 1/90* (2013.01); *C11D 1/94* (2013.01); *C11D 3/395* (2013.01); *C11D 3/3942* (2013.01); *C11D 3/43* (2013.01); *C11D 11/0017* (2013.01); *C11D 11/0023* (2013.01); *C07C 2601/16* (2017.05)

(58) Field of Classification Search
USPC ........................................................ 564/282
See application file for complete search history.

(56) References Cited

U.S. PATENT DOCUMENTS 3,336,387 A    8/1967   Finch et al.
4,207,260 A    6/1980   Imai
(Continued)

FOREIGN PATENT DOCUMENTS

CN    107028838 A      8/2017
JP    48039451    *    9/1973
(Continued)

OTHER PUBLICATIONS

Tolgyesi et al. Chemical Technology, 1971, 27-30.*
(Continued)

Primary Examiner — Ana Z Muresan
(74) Attorney, Agent, or Firm — Kenrick L. Vidale

(57) ABSTRACT

The surfactants which can be produced from the trialkylamine intermediates include the quaternary ammonium compounds of formula:

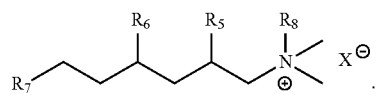

13 Claims, No Drawings

(51) Int. Cl.

| | |
|---|---|
| *A61Q 19/10* | (2006.01) |
| *C07C 211/04* | (2006.01) |
| *C07C 229/12* | (2006.01) |
| *C07C 309/14* | (2006.01) |
| *C07H 5/06* | (2006.01) |
| *C11D 1/90* | (2006.01) |
| *A01N 33/12* | (2006.01) |
| *B01J 31/02* | (2006.01) |
| *C07C 45/72* | (2006.01) |
| *C07C 209/22* | (2006.01) |
| *C07C 211/63* | (2006.01) |
| *C07C 211/64* | (2006.01) |

(56) References Cited

U.S. PATENT DOCUMENTS

| | | | |
|---|---|---|---|
| 4,276,205 | A | 6/1981 | Ferry |
| 4,292,242 | A | 9/1981 | Laine |
| 4,404,404 | A | 9/1983 | Swift et al. |
| 4,426,542 | A | 1/1984 | Barker et al. |
| 4,465,843 | A | 8/1984 | del Valle |
| 4,598,162 | A | 7/1986 | Forster et al. |
| 4,994,622 | A | 2/1991 | Fong et al. |
| 5,001,284 | A | 3/1991 | Dupont et al. |
| 5,030,774 | A | 7/1991 | Oswald et al. |
| 5,266,730 | A | 11/1993 | Abe et al. |
| 5,371,250 | A | 12/1994 | Seitz et al. |
| 5,491,240 | A | 2/1996 | Arnold et al. |
| 5,955,633 | A | 9/1999 | Prabhu |
| 6,037,497 | A | 3/2000 | Thomas et al. |
| 6,090,986 | A | 7/2000 | Godwin et al. |
| 7,049,270 | B2 | 5/2006 | Lennon et al. |
| 2004/0138510 | A1 | 7/2004 | Kramarz et al. |
| 2008/0167499 | A1 | 7/2008 | Molitor et al. |
| 2012/0157365 | A1 | 6/2012 | Fevola |

FOREIGN PATENT DOCUMENTS

| | | | |
|---|---|---|---|
| JP | H02160757 | A | 6/1990 |
| JP | H11279133 | A | 10/1999 |
| JP | 2014118385 | A | 6/2014 |
| WO | WO 85/02173 | A1 | 5/1985 |
| WO | WO 2003/091197 | A1 | 11/2003 |

OTHER PUBLICATIONS

Co-pending U.S. Appl. No. 16/243,229, filed Jan. 9, 2019; Clendennen et al.

Co-pending U.S. Appl. No. 16/243,232, filed Jan. 9, 2019; Clendennen et al.

Mills et al.; "Physical and Thermodynamic Properties for Novel $C_{14}$ Unsaturated Aldehydes and $C_{16}$ Saturated Amines;" J. Chem. Eng. Data; 1987; 32; pp. 251-265.

Fassbach et al.; "Renewable Surfactants through the Hydroaminomethylation of Terpenes;" ChemCatChem; 2017; 9; pp. 1359-1362.

Gomez et al.; "The Reductive Amination of Aldehydes and Ketones and the Hydrogenation of Nitriles: Mechanistic Aspects and Selectivity Control;" Adv. Synth. Catal.; 2002; 344; pp. 1037-1057.

Varjosaari et al.; "Simple Metal-Free Direct Reductive Amination Using Hydrosilatrane to Form Secondary and Tertiary Amines;" Adv. Synth. Catal.; 2017; 359; pp. 1872-1878.

Liang et al.; "$Au/TiO_2$ catalyzed reductive amination of aldehydes and ketones using formic acid as reductant;" Org. Chem. Front.; 2016; 3; pp. 505-509.

ASTM D2281-68; Standard Test Method for Evaluation of Wetting Agents by the Skein Test.

ASTM 4265; Standard Guide for Evaluating Stain Removal Performance in Home Laundering.

ASTM-E2407; Standard Test Method for Effectiveness of Defoaming Agents.

Moore et al.; "Role of the Surfactant Polar Head Structure in Protein—Surfactant Complexation: Zein Protein Solubilization by SDS and by $SDS/C_{12} E_n$ Surfactant Solutions;" Langmuir; 2003; 19; pp. 1009-1016.

Notification of Transmittal of the International Search Report and the Written Opinion of the International Searching Authority dated May 14, 2019 received in International Application No. PCT/US2019/012976.

\* cited by examiner

BRANCHED TRIALKYL QUATERNARY AMMONIUM COMPOUNDS

CROSS REFERENCE TO RELATED APPLICATIONS

This application claims priority under 35 U.S.C. 119(e) to U.S. Provisional Application Ser. No. 62/616,502 filed Jan. 12, 2018, which is incorporated herein by reference in its entirety.

FIELD OF THE INVENTION

The invention generally relates to the field of organic chemistry. It particularly relates to quaternary ammonium compounds, related branched trialkylamines, and products made therefrom, as well as branched enals or aldehydes, products made therefrom (including but not limited to branched trialkylamines) and methods of manufacturing all of these. It further relates to surfactants which include the quaternary ammonium compounds of the invention.

BACKGROUND OF THE INVENTION

There is a commercial need for novel surfactants with desirable properties such as low foaming, effective oily soil removal, performance in cold water, compatibility with other ingredients in a cleaning formula, mildness to skin, and a favorable environmental and safety profile.

A common trialkylamine hydrophobe used to make surfactants is dimethylalkylamine, made from C12 and C14 fatty alcohols reacted with dimethylamine, sometimes referred to as dimethyl laurylamine, or DIMLA. Neither DIMLA, its trialkylamine intermediate or the surfactants made from it contain branching.

Certain petrochemical detergent alcohols can also be used as surfactant hydrophobes. The most common synthetic detergent alcohols are produced by ethylene oligomerization, for instance, according to the Shell Higher Olefin Process (SHOP) process or the Ziegler alcohol process. Olefins can also be obtained from a Fischer-Tropsch process out of synthesis gas. The processing of producing detergent alcohols adds considerably to energy and facilities usage and consequently to product cost. Also, the resulting hydrophobes are typically over 85% linear.

Certain mixtures of C14 branched hydrophobes have also been described with some of the hydrophobe mixture containing a single branch point. When mixtures of hydrophobes are used to make surfactants, the individual hydrophobes in the mixture are not known to perform as well as the mixtures.

There remains a need in the industry for novel compositions which can be used to produce novel surfactants with desirable properties, for example, low foaming, mildness to skin, effective oily soil and/or stain removal (especially in cold water), high solubility in water, no gelling, ease of formulation, compatibilization or stabilization of other ingredients in a formula, retention of good hydrophobicity compared to linear hydrophobes, tolerance of extreme pH, antimicrobial activity, and/or a favorable environmental and safety profile. There also remains a need in the industry for effective reactants and processes to make branched surfactants and corresponding surfactant intermediates with fewer reaction byproducts, fewer reaction steps, and/or reduced reaction solvent(s).

SUMMARY OF THE INVENTION

In view of the above commercial shortcomings in the art, the present disclosure addresses the need for novel compositions, e.g., surfactants, with one or more of the following desirable properties: (1) low foaming, such as according to ASTM E2407, (2) mildness to skin, such as predicted by a zein solublization test or patch test, (3) effective oily soil and/or stain removal, especially in cold water, such as according to ASTM 4265, (4) compatibility with other ingredients in a cleaning formula, and (5) a favorable environmental profile, (6) high solubility in water; (7) no gelling, (8) ease of formulation, and (9) compatibilization or stabilization of other ingredients in a formula, (10) retains good hydrophobicity compared to linear hydrophobes, (11) tolerance of extreme pH, (12) antimicrobial activity, (13) biodegradability, such as according to OECD 301B and/or (14) an improved safety profile. The compositions of this invention can provide desirable properties for a variety of applications.

The invention is as set forth in the Field of the Invention, the Summary of the Invention, the Description, the Examples, the appended Claims, and the Abstract.

For the ease of reference but not intending to be limiting in any way, certain aspects of this disclosure are numbered consecutively, as follows:

In aspect 1, this invention provides at least one quaternary ammonium compound comprising the following formula:

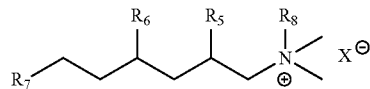

wherein R8 is methyl, ethyl, butyl, or benzyl, and X is a halide or alkosulfate,
wherein R5, R6 and R7 are independently at least one of C3H7, C2H5, CH3, or H; and
wherein R5 and R6 are not H at the same time.

In aspect 2, this invention provides the quaternary ammonium compound of aspect 1 comprising the formula:

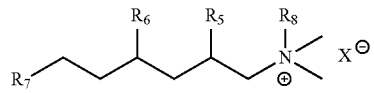

wherein R5 and R6 are C3H7, C2H5, CH3, or combinations thereof; and
wherein R7 is one of C3H7, C2H5, CH3, H or combinations thereof.

In aspect 3, this invention provides the quaternary ammonium compounds of any one of aspects 1-2 wherein R6 is CH3 or C2H5.

In aspect 4, this invention provides the quaternary ammonium compound of aspect 1-3 wherein R5 is CH3 or CH2H5.

In aspect 5, this invention provides the quaternary ammonium compound of aspect 1-4 wherein R5 is CH3 and R6 is C2H5 or wherein R5 is C2H5 and R6 is CH3.

In aspect 6, this invention provides the quaternary ammonium compounds of any one of aspects 1-4 wherein R5 and R6 independently are each C2H5; or wherein R5 and R6 independently are each CH3.

In aspect 7, this invention provides the quaternary ammonium compound of any one of aspects 1-6 wherein R8 is benzyl or butyl.

In aspect 8, this invention provides the quaternary ammonium compound of any one of aspects 1-7 wherein X— is halide.

In aspect 9, this invention provides the quaternary ammonium compound of aspect 8 wherein the halide is selected from chloride, bromide or iodide.

In aspect 10, this invention provides the quaternary ammonium compound of any one of aspects 1-9 selected from N-benzyl-2,4-diethyl-N,N-dimethyloctan-1-aminium chloride or N-butyl-2,4-diethyl-N,N-dimethyloctan-1-aminium bromide.

In aspect 11, this invention provides a composition comprising at least one quaternary ammonium compound of any one of aspects 1-10.

In aspect 12, this invention provides a composition comprising at least one quaternary ammonium compound of aspect 11 wherein quaternary ammonium compounds other than those of any one of aspects 1-11 are excluded.

In aspect 13, this invention provides the composition of any one of aspects 11-12 comprising at least one nonionic surfactant, anionic surfactant, cationic surfactant, amphoteric surfactant, or combinations thereof.

In aspect 14, this invention provides the composition of any one of aspects 11-13 comprising 0.01% to 30% by weight of said quaternary ammonium compound based on the total weight of the composition equaling 100 weight %.

In aspect 15, the invention provides a composition selected from any one of aspects 11-14 wherein the trialkylamine(s) used to make the quaternary ammonium compound(s) does not contain any isomeric compound or mixtures, wherein said mixtures can contain a number of isomeric compounds, and wherein said isomeric compound(s) can be selected from those of structures:

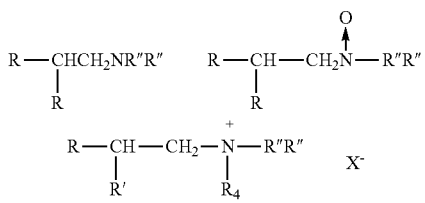

having from 10 to 18 carbon atoms in the R(R')CHCH2-moiety in which R has 5 to 9 carbon atoms, and R' has from 3 to 7 carbon atoms, with most of the compounds having additional methyl or ethyl branches, and in which R' and R" are alkyl or hydroxyalkyl groups or hydrogen and X— is an anion.

In aspect 16, the invention provides a composition of aspect 15 wherein the trialkylamine(s) used to make the quaternary ammonium compound(s) does not contain any isomeric compound or mixture of isomers of aspect 15, wherein said mixtures can contain a number of isomeric compounds, wherein said isomeric compound(s) can be selected from tertiary amines with a higher branched-chain alkyl substituent characterized as having 10 to 18 carbon atoms and an alkyl branch at the 2-position containing 3 to 7 carbon atoms, and additional branching in most of the isomers, with most of the additional branches being methyl groups.

In aspect 17, the invention provides a composition selected from any one of aspects 11-15 wherein the trialkylamine(s) used to make the quaternary ammonium compound(s) of the invention does not contain any isomers or mixtures of isomers of any one of aspects 15 or 16, wherein said mixtures contain a number of isomeric compounds, and wherein said isomeric compounds can be selected from tertiary amines with a higher branched-chain alkyl substituent characterized as having 12 carbon atoms and an alkyl branch at the 2-position containing 5 carbon atoms or greater, whether or not with additional branching in most of the isomers, whether or not with most of the additional branches are methyl groups and/or ethyl groups.

In aspect 18, the invention provides a composition comprising at least one quaternary ammonium compound wherein the composition is selected from any one of aspects 11-14 but which does not contain any quaternary ammonium compound or mixtures of quaternary ammonium compounds other than those described or referred to in aspects 11-14 or otherwise described within the scope of this invention.

In aspect 19, the invention provides at least one quaternary ammonium compound (for example, the compounds of any one of aspects 1-10) or composition(s) comprising said quaternary ammonium compound (for example, the compositions of aspects 11-18), any of which can be a disinfecting agent.

In aspect 20, the invention provides at least one quaternary ammonium compound or composition of aspect 19 having a minimum lethal concentration against at least one microbe selected from gram-positive bacteria, gram-negative bacteria, and/or yeast, when used at concentrations of less than 200 ppm, or less than 150 ppm, less than 100 ppm, or less than 75 ppm, or less than 65 ppm.

In aspect 21, the invention provides at least one quaternary ammonium compound or composition of aspect 20 having a minimum lethal concentration against E. coli, S. aureus and/or C-albicans when used at concentrations of less than 200 ppm, or less than 150 ppm, less than 100 ppm, or less than 75 ppm, or less than 65 ppm.

In aspect 22, the invention provides at least one quaternary ammonium compound or composition of aspect 21 having a minimum lethal concentration against E. coli, S. aureus and/or C-albicans when used at concentrations of less than 200 ppm, or less than 150 ppm, less than 100 ppm, or less than 75 ppm wherein the quaternary ammonium compound is N-benzyl-2,4-diethyl-N,N-dimethyloctan-1-aminium chloride.

In aspect 23, the invention provides one or more phase transfer catalysts comprising at least one quaternary ammonium compound of any one of aspects 1-10 or 20-22.

In aspect 24, the invention provides at least one process for using at least one quaternary ammonium compound of any one of aspects 1-10 or 20-22.

In aspect 25, the invention provides at least one process for using at least one quaternary ammonium compound of any one of aspects 1-10 or 20-22 as a phase transfer catalyst.

In aspect 26, the invention provides at least one process of aspect wherein said phase transfer catalyst is used in a process for making a enal or aldehyde, whether branched or not, for example, any enal or aldehyde useful in making any product of this invention, for example, products including but not limited to trialkylamines (including branched or non-branched trialkylamines), amino acids, sarcosine product, glucamine products, trialkylamine oxides, quaternary ammonium compounds, carboxybetaines, and/or hydroxysultaines of the invention.

In aspect 27, the invention provides at least one process of making a quaternary ammonium compound.

In aspect 28, this invention provides the process of any one of aspects 27 wherein the alkylating agent selected to make the quaternary ammonium compound is selected from at least one of C1-C4 alkyl chloride, C1-C4 alkyl bromide or C1-C4 alkyl iodide, benzyl chloride, benzyl bromide or benzyl iodide, or combinations thereof.

In aspect 29, this invention provides the quaternary ammonium compound of aspect 28 wherein the alkylating agent can be selected from at least one of methyl chloride, ethyl chloride, propyl chloride, butyl chloride, methyl bromide, ethyl bromide, propyl bromide, butyl bromide, benzyl chloride, benzyl bromide or combinations thereof.

In aspect 30 this invention provides the quaternary ammonium compound of aspect 27-29 wherein the halide is C1-C4 alkyl bromide.

In aspect 31, this invention provides the quaternary ammonium compound of aspect 30 wherein the alkyl bromide is butyl bromide or any isomers thereof.

In aspect 32, this invention provides processes for making the trialkylamines useful in the invention made from the branched enals and aldehydes useful in the inventon.

In aspect 33, the invention provides branched enals and aldehydes made using the quaternary ammonium compounds of the invention and processes for making these branched enals and aldehydes.

In aspect 34, the branched enals and aldehydes useful in the invention can optionally be made when the quaternary ammonium compounds of this invention are phase transfer catalysts.

In aspect 35, aldehydes useful in making the trialkylamines useful in the present invention and/or made using the quaternary ammonium compounds of the invention of any one of aspects 1-10 or 20-22 can contain aliphatic hydrocarbon chains, linear or branched, saturated or unsaturated, comprising 2 to 30 carbon atoms.

In aspect 36, aldehydes useful in making the trialkylamines useful in the present invention and/or made using the quaternary ammonium compounds of the invention of any one of aspects 1-10 or 20-22, for example, can be branched C8-C20 aldehydes, for example, 2-ethylhexanal, 2-propylpentanal, 2-propyl-hexanal, 2-propyl-heptanal, 2-propyl-octanal, 2,4-diethyloctanal, 2-ethyl-4-methyl-nonanal, 2-ethyl-4-methyloctanal, or 2-butyl-4-ethyloctanal or combinations thereof.

In aspect 37, examples of enals or aldehydes useful in making any one of the trialkylamines useful in the invention and/or made using the quaternary ammonium compounds of the invention of aspects 1-10 or 20-22, for example, include but are not limited to as follows: Examples of C10 to C12 enals include but are not limited to: 4-ethyl-2-methyloct-2-enal (C11 enal), 2,4-diethyl-2-octenal (C12 enal), 2-propyl-heptenal (C10 enal), or 2-ethyl-4-methyl heptenal (C10 enal); Examples of C10 to C12 aldehydes include but are not limited to: aldehyde-4-ethyl-2-methyloctanal (C11 aldehyde), 2,4-diethyl-2-octanal (C12 aldehyde); 2-propyl-heptanal (C10 aldehyde), and 2-ethyl-4-methyl heptanal (C10 aldehyde).

In aspect 38, the invention provides a process for making a quaternary ammonium compound comprising using a trialkylamine having the formula:

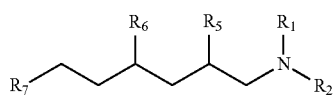

wherein R1 and R2 are each independently selected from straight or branched chain or cyclic hydrocarbon radicals having 1 to 8 carbon atoms;
wherein R5, R6 and R7 are independently at least one of C3H7, C2H5, CH3, or H, or combinations thereof; and wherein R5 and R6 are not H at the same time.

In aspect 39, the invention provides the process of aspect 38 wherein, for the trialkylamine, (a) R1 and R2 are each independently substituted with groups selected from: —OR3; carboxyl; —NHCOR4; —CONHR4; cyano; —CO2R3; —OCOR3; hydroxy; aryl; heteroaryl; chlorine; or a combination thereof, (b) R3 is selected from C1-C6 alkyl, substituted C1-C6 alkyl or combinations thereof and (c) R4 is selected from C1-C4 alkyl or substituted C1-C15 alkyl.

In aspect 40, the invention provides the processes of aspects 38 or 39 wherein the trialkylamines are selected from the group consisting of alkyl dimethyl amines or N,N-dimethylalkylamines.

In aspect 41, the invention provides the process of any one of aspects 38-40 wherein, for the trialkylamine, R1 can be CH3 or C2H5 and/or R2 can be CH3 or C2H5.

In aspect 42, the invention provides the process of aspect 41 wherein R1 is CH3.

In aspect 43, the invention provides the process of aspects 41 or 42 wherein R2 is CH3.

In aspect 44, the invention provides the processes of aspects 41 or 43 wherein R1 can be C2H5.

In aspect 45, the invention provides the process of aspects 41 or 42, wherein R2 can be C2H5, or of aspect 44, wherein R1 and R2 can each independently be C2H5.

In aspect 46, the invention provides the or process of any one of aspects 38-40, 42 or 44 wherein R1 is CH3 or C2H5 and R2 is a carbohydrate or amino acid.

In aspect 47, the invention provides the process of any one of aspects 38-46 wherein R5 and R6 are C3H7, C2H5, CH3, or combinations thereof; and wherein R7 is one of C3H7, C2H5, CH3, H or combinations thereof.

In aspect 48, the invention provides the process of aspect 47 wherein R5 is CH3 or C2H5 and/or R6 is CH3 or C2H5.

In aspect 49, the invention provides the process of any one of aspects 47-48 wherein R5 is CH3.

In aspect 50, the invention provides the process of any one of aspects 47-49 wherein R6 is CH3.

In aspect 51, the invention provides the process of aspects 47, 48 or 50 wherein R5 can be C2H5.

In aspect 52, the invention provides the process of aspects 47-49 or 51 wherein R6 can be C2H5.

In aspect 53, the invention provides the process of any one of aspects 38-52 wherein the trialkylamine has one to three branch points.

In aspect 54, the invention provides the trialkylamine of any one of aspects 38-53 wherein the trialkylamine has one to three branch points at the R5 and/or R6 positions; in one embodiment, where the trialkylamine has three or greater than three branch points, up to two of the branch points can be at the R5 and/or R6 positions.

In aspect 55, the invention provides the process of any one of aspects 38-54 wherein the trialkylamine has two branch points which are at the R5 and R6 positions.

In aspect 56, the invention provides the process of any one of aspects 38-55 wherein the number of carbon atoms for the alkyl substituent at the R5 position of the trialkylamine can be from one to three.

In aspect 57, the invention provides the process of any one of aspects 38-56 wherein the number of carbon atoms for the alkyl substituent at the R6 position of the trialkylamine can be from one to three.

In aspect 58, the invention provides the process of any one of aspects 38-57 wherein the number of carbon atoms for the alkyl substituent at the R5 position of the trialkylamine can be from one to two.

In aspect 59, the invention provides the process of any one of aspects 38-58 wherein the number of carbon atoms for the alkyl substituent of the trialkylamine at the R6 position can be from one to two.

In aspect 60, the invention provides at least a process for making at least one quaternary ammonium compound from at least one trialkylamine selected from 4-ethyl-N,N,2-trimethyloctan-1-amine, 4-ethyl, 2-methyl, N,N-dimethylhexan-1-amine, or 2,4-diethyl, N,N-dimethyloctan-1-amine.

In aspect 61, the invention provides a composition comprising any one of the quaternary ammonium compounds of the invention or useful in the invention.

In aspect 62, the invention provides a composition comprising at least one quaternary ammonium compound derived from any trialkylamine or trialkylamine combination described in the process of any one of aspects 38-60 but which trialkylamine or trialkylamine combination does not contain any isomeric compound or mixtures wherein said mixtures contain a number of isomeric compounds, and wherein said isomeric compound(s) can be selected from those of structures:

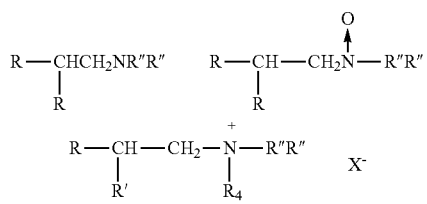

having from 10 to 18 carbon atoms in the R(R')CHCH2- moiety in which R has 5 to 9 carbon atoms, and R' has from 3 to 7 carbon atoms, with most of the compounds having additional methyl or ethyl branches, and in which R' and R" are alkyl or hydroxyalkyl groups or hydrogen and X— is an anion.

In aspect 63, the invention provides a composition comprising at least one quaternary ammonium compound which is not derived from any trialkylamine(s) or trialkylamine combinations, which does not contain any isomeric compound or mixture of isomers described in aspect 62, wherein said mixtures contain a number of isomeric compounds, wherein said isomeric compound(s) can be selected from tertiary amines with a higher branched-chain alkyl substituent characterized as having 10 to 18 carbon atoms and an alkyl branch at the 2-position containing 3 to 7 carbon atoms, and additional branching in most of the isomers, with most of the additional branches being methyl groups.

In aspect 64, the invention provides a composition comprising at least one quaternary ammonium compound which is not derived from any trialkylamine(s) or trialkylamine combinations containing any isomers or mixtures of isomers of aspects 62 or 63, wherein said mixtures contain a number of isomeric compounds, and wherein said isomeric compounds can be selected from tertiary amines with a higher branched-chain alkyl substituent characterized as having 12 carbon atoms and an alkyl branch at the 2-position containing 5 carbon atoms or greater, whether or not with additional branching in most of the isomers, whether or not with most of the additional branches are methyl groups and/or ethyl groups.

In aspect 65, the invention provides a composition comprising at least one quaternary compound which is not derived from any trialkylamine or combinations of trialkylamines other than those described herein as being within the aspects of this Summary of the Invention or as otherwise described within the scope of this invention.

In aspect 66, this invention provides home care products, industrial cleaners, agrochemical formulations, coatings, fuel treatments, oil cleaners, oil recovery, oil dispersants, disinfectants, water treatments, bleaches, detergents, stain removers, soap, oily soil cleaner, grease cutter, soft surface cleaners or hard surface cleaners comprising the composition of any one of aspects 11-22 or 61-6 and/or the quaternary ammonium compounds of any one of aspects 1-10, or 20-22.

In aspect 67, this invention provides dish detergents, kitchen surface cleaners, bathroom surface cleaners, upholstery cleaners, laundry stain remover, carpet cleaner, carpet spot remover, or laundry detergents comprising the composition of any one of aspects 11-22 or 61-66 and/or the quaternary ammonium compounds of any one of aspects 1-10, or 20-22.

In aspect 68, this invention provides at least one amine quaternary ammonium compound made from any one of the trialkylamines of any one of the processes of aspects 38-60.

In aspect 69, the invention provides a composition comprising at least one quaternary ammonium compound and/or at least one trialkylamine oxide, each independently made from any one of the trialkylamines described in any one of the processes of aspects 38-60.

DETAILED DESCRIPTION OF THE INVENTION

In The present invention may be understood more readily by reference to the following detailed description of certain embodiments of the invention and the working examples. In accordance with the purpose(s) of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifications and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

As used in the specification and the appended claims, the singular forms "a," "an" and "the" include their plural referents unless the context clearly dictates otherwise. The terms "containing" or "including" are intended to be synonymous with the term "comprising", meaning that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

Also, it is to be understood that the mention of one or more process steps does not preclude the presence of additional process steps before or after the combined recited steps or intervening process steps between those steps expressly identified.

In one embodiment, this invention provides novel compositions which can be used to produce novel surfactants. This invention also provides effective reactants and processes to make the branched surfactants and corresponding surfactant intermediates with fewer reaction byproducts, fewer reaction steps, and/or reduced reaction solvent.

As used herein the term "hydrophobe" means a molecule that can serve as the hydrophobic, or non-polar segment of a surface-active compound or surfactant. The branched $C_{10}$-$C_{12}$ hydrophobes useful in this invention and their surfactant derivatives are often liquids at room temperature, the surfactants are typically low foaming and may be mild to skin. Surfactants made from the branched hydrophobes can have improved solubility in water and can interact differently with other ingredients in a formulation. They can also have altered biological activity that can provide beneficial activity (such as antimicrobial, antifungal, and/or antiviral activity) or safety (such as reduced aquatic toxicity, reduced skin irritation, reduced irritation to eyes and mucous membranes, reduced allergenicity or tendency to cause contact dermatitis). As a result, the surfactants derived from branched trialkylamine hydrophobes can have properties well-suited for use in personal and home care applications, which value these traits in formulating, use and disposal of the surfactants.

In one embodiment, this invention provides novel compositions which can be used to produce other novel compositions, e.g., surfactants, or which can be surfactants themselves, having one or more of the following desirable properties: (1) low foaming, such as according to ASTM E2407, (2) mildness to skin, such as predicted by a zein solublization test or patch test, (3) effective oily soil and/or stain removal, especially in cold water, such as according to ASTM 4265, (4) compatibility with other ingredients in a cleaning formula, and (5) a favorable environmental profile, (6) high solubility in water; (7) no gelling, (8) ease of formulation, and (9) compatibilization or stabilization of other ingredients in a formula, (10) retains good hydrophobicity compared to linear hydrophobes, (11) tolerance of extreme pH, (12) antimicrobial activity, (13) biodegradability, such as according to OECD 301B and/or (14) an improved safety profile. This invention also provides effective reactants and processes to make branched surfactants and corresponding surfactant intermediates with fewer reaction byproducts, fewer reaction steps, and/or reduced reaction solvent.

In one embodiment, the compositions of this invention can provide one or more of the following properties: (1) low foaming, (2) effective oily soil and/or stain removal, especially in cold water, (3) high solubility in water; (4) no gelling, (5) ease of formulation, (6) compatibilization or stabilization of other ingredients in a formula, (7) tolerance of extreme pH, (8) biodegradability, (9) antimicrobial activity, and/or (10) an improved safety profile.

Low foaming characteristics in combination with improved cleaning performance such as more effective soil and/or stain removal is important for laundry and dishwashing formulations where low foaming results in greater efficiency and durability of dishwashers, washing machines, upholstery and rug cleaners or other appliances utilizing them. Also, higher solubility in water and/or no gelling enable the compositions of the invention to be placed in a more concentrated liquid form prior to transfer, transport for both reactions and formulations. Branched surfactants can also reduce the viscosity of the formulation(s) that they are in which can provide benefits like easier dispensing and reduction in the requirement for added water in the formulation.

The invention provides novel branched hydrophobes for the production of surfactants with altered properties over typical linear hydrophobes. In one embodiment, the invention provides trialkylamine hydrophobes. In another embodiment, the invention provides branched enals and aldehydes which are useful in making the trialkylamines useful in the invention, the N-alkyl-N glucamines, and/or the alkyl-N-sarcosines of the invention. The trialkylamines useful in the invention can be used in making the quaternary ammonium salts or "quats", alkyl betaines or alkyl hydroxysultaines, and/or trialkylamine oxides of the invention.

In another embodiment, the invention provides a process for making the branched enals and aldehydes, surfactant intermediates or surfactants that reduces or eliminates the formation of byproducts, reduces process steps or reaction solvent.

In another embodiment, the invention provides branched enals and aldehydes that are oxidized to branched fatty acids or hydrogenated to branched fatty alcohols and further derivatized to surfactants, through ethoxylation or esterification and other or subsequent reactions. The invention also provides surfactants made from the branched trialkylamine intermediates, including amphoteric, cationic and nonionic surfactants.

In the present invention, enals and aldehydes with more than one branch point useful in the invention can be produced by a combination of hydroformylation and aldol condensation. In one embodiment, the enals and aldehydes can have two branch points. For example, 2-ethylhexanal can be reacted with either propionaldehyde or n-butyraldehyde in a crossed aldol reaction to produce a C11 or C12 enal. Alternately, the self-condensation product of propionaldehyde can be reacted with n-butyraldehyde to produce a C10 enal with two branch points. Examples of the reactions and products are depicted below. The C10 to C12 enals can be further hydrogenated to the corresponding aldehyde or alcohol.

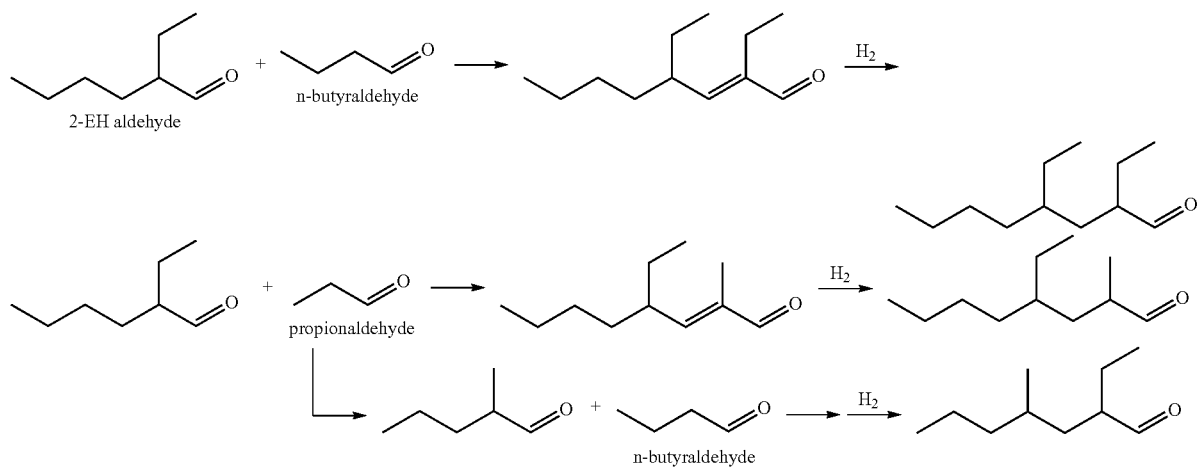

Aldol condensation reactions, or aldolization reactions, are known in the art. Two types of aldol condensation reactions frequently encountered are the self-aldol condensation (Aldol I) and cross-aldol condensation (Aldol II) reactions. In an Aldol I reaction, two molecules of the same aldehyde starting material react to form a reaction product. Alternatively, in an Aldol II reaction, two different aldehyde starting materials react to form a reaction product.

The reaction between two of the same aldehyde molecules is a classic case with an equilibrium far to the right. In practice, the condensation of two molecules of the same aldehyde (Aldol I) to form an aldol can be followed immediately by dehydration to form an unsaturated aldehyde with twice the original number of carbon atoms.

In an Aldol II reaction, however, the condensation of two molecules of different aldehydes forms an aldol and, upon dehydration, further forms an unsaturated aldehyde having the sum of the carbon atoms of the two different aldehydes. Both Aldol I and Aldol II reactions are well known in the art, as are the conditions required to affect their condensation.

The C10 to C12 aldehydes useful in the invention are formed by reacting at least one aldehyde starting material in the presence of a basic catalyst to form aldol condensation products.

In one embodiment, the aldehyde starting materials can include but are not limited to C2 to C8 aldehydes selected from the group consisting of acetaldehyde, propionaldehyde, n-butyraldehyde, isobutyraldehyde, valeraldehyde, 2-ethylbutyraldehyde, 2-methylpentanal, 2-ethylhexanal or combinations thereof. although other aldehydes can also be suitable.

The aldol condensation can be enacted in a single step, as in the crossed aldol reaction of n-butyraldehyde and 2-ethylhexanal, or in more than one step, as in the aldol condensation or propionaldehyde to form 2-methyl-2-pentenal followed by hydrogenation to 2-methylpentanal, then a crossed aldol reaction between 2-methylpentanal and n-butyraldehyde to form 2,4-dimethyl-2-heptenal. U.S. Pat. No. 6,090,986 to Godwin et al. discloses an example of Aldol II in the formation of 2,4-dimethyl-2-heptenal from condensing 2-methyl-pentanal and propanal.

The cross aldol or homoaldol reactions run in utilization of this invention can be catalyzed by the addition of a base. A base can be defined in many ways such as any substance that releases hydroxide ions (OH⁻) upon dissolution in water or a substance that accepts a proton (Bronsted-Lowry theory). A base can also be any substance that donates an electron pair (Lewis Theory) [Whitten and Gailey, 1981].

In the invention, the aldol reactions can be catalyzed by any substance or substances meeting any of the definitions described herein or in the art of a base. In the invention, the aldol reactions can be catalyzed by any substance or substances meeting any of the definitions described herein or in the art of a base. In one embodiment, the base can be any hydroxide, bicarbonate, or carbonate salt of the Group I or Group II metals; NaOH; KOH; NaHCO$_3$; Na$_2$CO$_3$; LiO; CsOH; sodium methoxide; sodium ethoxide; sodium propoxide; potassium methoxide; potassium butoxide; cesium methoxide, or the like, or combinations thereof. In one embodiment, the catalysts can include NaOH, NaHCO3, KOH, or K2CO3.

In one embodiment, the base can be any hydroxide, bicarbonate, or carbonate salt of the Group I or Group II metals. In another embodiment, the base can be one or more selected from NaOH, KOH, NaHCO$_3$, Na$_2$CO$_3$, LiOH, CsOH, and the like. In another embodiment, the basic catalyst (base) can also be chosen from sodium methoxide, sodium ethoxide, sodium propoxide, potassium methoxide, potassium butoxide, cesium methoxide, or the like. In another embodiment, the base is NaOH. When the base is NaOH, using a ratio of 1.15 to 1.25 of NaOH:nHbu can provide an enal yield of at least 40%.

The catalyst can also be other organic or inorganic bases and can, for example be carbonates, bicarbonates, phosphates, pyrophosphates, and hydrogenphosphates of alkali metals, and/or it may include quaternary ammonium compounds, tertiary amines, ion exchange resins, guanidine derivatives, amidine compounds, and combinations thereof. In one embodiment, tertiary amines can be the catalyst. In another embodiment, the catalyst can be NaOH. The concentration of the basic catalyst can be varied, but molar or similar concentrations of alkali metal hydroxides can be used, and concentrations selected will generally be in the range of about 1 to 50% or 1 to 30% or 1 to 25% 5 to 50% or 5 to 30% or 5 to 25% by weight based on the total weight of the composition. The amount of aqueous alkali to aldehyde reactant can also vary, for example, from about 15% by volume aqueous alkali up to about 75% by volume aqueous alkali. In one embodiment, the amount of aqueous alkali to aldehyde reactant can also vary, for example from about 20% by volume aqueous alkali up to about 45% by volume aqueous alkali. In yet another embodiment, the amount of aqueous alkali to aldehyde reactant can also vary, for example, from about 25% by volume aqueous alkali up to about 35% by volume aqueous alkali.

The base catalyst, especially the most commonly used bases, NaOH, KOH, NaHCO$_3$, and the like, are introduced as aqueous solutions to the reaction mixture. As the chain length of the raw material aldehyde or ketone increases, the solubility of the base in the organic reaction medium can decrease. For instance, two molecules of 4 carbon n-butyraldehyde readily react in aqueous caustic, but one molecule of n-butyraldehyde and one molecule of 8 carbon 2-ethylhexanal may not react in the same basic solution. In order to increase the solubility of the longer chain molecule, a phase transfer catalyst (PTC) is used.

Phase transfer catalysts shuttle ions across organic and aqueous phase boundaries. A phase transfer catalyst (PTC) is effective in improving conversion in this procedure. In many cases, the phase transfer catalyst is a quaternary ammonium salt. The PTC can be any quaternary ammonium salt capable of transmitting organic and aqueous components across a phase boundary. The quaternary ammonium salt could be a pure component or a mixture of salts. Typical quaternary ammonium salts are comprised of tetra alkyl or tetra aromatic ammonium cations and a counter anion. Counter anions include halogens or polyatomic ions such as $BF_4$, $PF_6$, $SO_2$, $SO_4$, or the like. Common PTCs include tetrabutyl ammonium chloride, tetrabutyl ammonium bromide, tetrabutyl ammonium iodide, tetramethyl ammonium chloride, and benzalkyl ammonium chloride. The use of co-solvents, such as methanol or diols, may also be used. The concentration of PTC can vary.

To avoid the formation of byproducts, such as Hoffman Elimination byproducts, from PTC such as tetrabutyl ammonium salts or combinations of alkyl benzyl ammonium salts, this invention provides a phase transfer catalyst utilizing an amine derived from the aldehydes useful in the invention, for example, a C10, C11 or C12 aldehyde. For example, 2,4-diethyl-octenal, produced by the cross aldol reaction of n-butyraldehyde and 2-ethylhexanal, can be combined with N,N-diethylamine over a copper catalyst to produce 2,4-diethyl-N,N-dimethyloctan-1-amine. The product amine can then be reacted with benzyl chloride to form the PTC in excellent yield. Similarly, the product amine can be reacted with an alkyl chloride (ethyl chloride, propyl chloride, butyl chloride) to generate a PTC. In one embodiment, one quarternary ammomium salt of the invention is N-benzyl-2,4-diethyl-N,N-dimethyl-octyl ammonium chloride.

The resultant phase transfer catalyst is similar in structure to any of the components of the mixture alkyldimethylbenzylammonium chloride, but is comprised of a single molecule. Its resultant use in cross aldol reactions can deliver similar or superior yields to BAC and to other PTCs described in the art, with the added benefit of producing a single high boiler component as identified by gas chromatography. The aldol products are easily separated from this single high boiler by distillation.

In one embodiment, the PTC useful in the invention can be used in the cross aldol reaction of n-butyraldehyde and 2-ethylhexanal to produce 2,4-diethyloctenal in reasonable yield. The PTC can also be used in any aldol condensation involving any two aldehydes compound containing a carbon chain from 1-20 carbons. Such aldehydes include formaldehyde, acetaldehyde, propionaldehyde, butyraldehyde, 2-methyl-propionaldehyde, valeraldehyde (1-pentanal), isovaleraldehyde (2-methyl-butyraldehyde), hexanal, 2-ethylhexanal, 1-octanal, 1-nonanal, and the like. The reaction utilizing this invention can contain two or more different aldehydes (cross aldol) of two or more molecules of the same aldehyde (homoaldol).

The aldol condensation reaction can be performed in an aqueous solution, in an organic solvent, or in a mixture of water and an organic solvent. Such organic solvents include methanol, ethanol, propanol, butanol, acetone, acetonitrile, pentane, hexane, heptane, cyclohexane. The solvent can also be any of the starting aldehydes or product aldehydes useful in the invention.

The reactions for forming aldol condensation products can be generally carried out at a pressure of from about 1 atm (atmospheric pressure) to about 1000 atm (elevated pressure) or from about 1 atm to about 500 atm or from about 1 to about 300 atm or from about 1 to about 100 atm or from about 1 to about 50 atm or from about 1 to about 20 atm. The reaction can be carried out over a wide range of temperatures and is not particularly limited. The reaction temperature can be within the range of from about −20° C. to 300° C., for example, within the range of from 20° C. to 100° C.

The reaction can be run at ambient temperature and pressure. Increased conversion can be accomplished by running at higher temperature or pressure. In one embodiment, the reaction can be run between 20° C. and 70° C. In another embodiment, the reaction can be run between 50° C. and 70° C.

The reaction temperature can be increased by running the reaction at higher pressures. In one embodiment, the reaction can be run anywhere from 100 kPa to 2000 kPa. In another embodiment, the reaction can be run from 100 to 1000 kPa. In yet another embodiment, the reaction can be run at ambient (atmospheric) pressure.

The aldol reaction can be run for a sufficient time to obtain the desired degree of conversion. The aldol condensation reactions can run for about 1 to 10 hours or 1 to 3 hours. They can be run as batch or continuous reactions. When run as continuous reactions, the residence time can be substantially shorter than 3 hours, for example, less than 2 hours, less than 1 hour, less than 30 minutes, less than 10 minutes, or less than 5 minutes. In one embodiment, batch reactions can be run in the range of about 30 minutes to about 3 hours or about 1 to about 3 hours.

The reaction can be stopped by permitting the reaction mixture to cool and separating the organic reaction phase from the aqueous alkali phase. The saturated or unsaturated aldehyde can be purified prior to further conversion, or may be used directly. Purification of the saturated or unsaturated aldehyde can be effected by decanting, extraction, distillation, filtration or chromatographic separation.

Following the aldol condensation step, the unsaturated product can be hydrogenated to produce the saturated aldehyde, which can be further hydrogenated to form the alcohol or, alternatively, can be oxidized to form the carboxylic acid. The unsaturated aldehyde or enal can be used directly as a substrate for reductive amination.

The branched C10 through C12 enals and aldehydes produced in the present process or otherwise useful in this invention can be especially suitable for conversion to other useful compositions. The present invention provides unsaturated and saturated aldehydes which can be converted to the corresponding saturated or unsaturated alcohols or acids, and further derivatized to form surfactants, such as alcohol ethoxylates or fatty acid esters, or sulfated or sulfonated forms of these molecules. The reactions can be effected at the enal stage, or with the saturated aldehydes.

Examples of C10 to C12 enals useful in this invention include but are not limited to: 4-ethyl-2-methyloct-2-enal (C11 enal), 2,4-diethyl-2-octenal (C12 enal), 2-propyl-heptenal (C10 enal), or 2-ethyl-4-methyl heptenal (C10 enal); Examples of C10 to C12 aldehydes include but are not limited to: aldehyde-4-ethyl-2-methyloctanal (C11 aldehyde), 2,4-diethyl-2-octanal (C12 aldehyde); 2-propyl-heptanal (C10 aldehyde), and 2-ethyl-4-methyl heptanal (C10 aldehyde).

Examples of products that can be made with the C10 to C12 enals and/or aldehydes useful in the invention are as follows: (A.) N-alkyl-N-methylglucamines: the C10 through C12 enals and aldehydes useful in this invention can be reacted with N-methylglycamines to generate sugar-based surfactants. For example, the C10 through C12 enals and aldehydes can be reacted with N-methylglucamine to generate N-alkyl-N-methylglucamines. Similarly, the C10 through C12 enals and aldehydes can be reacted with N-methyl amino acids to afford an amino acid based surfactant; (B.) Sarcosines: For example, the C10 through C12 enals and aldehydes described herein can be reacted with N-methylglycine to generate alkyl-N-sarcosines; (C.) Trialkylamines: The C10 to C12 enal or aldehydes described herein may be reacted with dialkyl amines such as dimethylamine to obtain N,N-dimethylalkylamines as surfactant intermediates. Similarly, the C10 to C12 enal or aldehydes can be reacted with diethanolamine, dipropylamine, diisopropylamine to obtain the corresponding trialkylamine. The trialkylamines decribed herein can be used to make other products, for example, (D.) Amphoterics: Betaines, including Carboxybetaines; and Hydroxysultaines; (E.) Quaternary Ammonium Compounds; (F.) Trialkylamine Oxides; as well as others compounds. The trialkylamines of the invention can are described in more detail as follows:

In one embodiment, the C10 to C12 enal or aldehydes useful in the invention can be reacted with dialkyl amines such as dimethylamine to obtain N,N-dimethylalkylamines which can be useful, for example, as surfactant intermediates. Similarly, the C10 to C12 enal or aldehydes can be reacted with diethylamine, dipropylamine, or diisopropylamine to obtain the corresponding trialkylamines.

Among the more versatile surfactant intermediates are the trialkylamines, also called tertiary amines. In the present invention, C10 to C12 enals or aldehydes are reacted with a secondary amine under reductive conditions to produce trialkylamines useful in the invention.

Reductive amination processes are well known in the art for the synthesis of primary, secondary and tertiary amine. The term "amination" relates to the reaction part in which an amine functionality is incorporated into the substrate. The term "reductive" relates to the observation, when comparing the feed substrate and the product of a reductive amination reaction, that a reduction has necessarily also taken place. In chemistry, a reduction reaction refers in general to the gain of electrons of an atom or a molecule. In organic chemistry, reductions are usually related with the disappearance of unsaturated functionality, such as double bonds, from the substrate molecules. The net result of a reductive amination of a ketone or aldehyde is the conversion of a C=O double bond into a C—N single bond.

The reductive amination of ketones or aldehydes towards trialkylamines can be done in either one or two process steps in which the first step comprises the reaction of the ketone or aldehyde with an amination reagent such as dimethylamine to form an intermediary imine or enamine followed by the second process step in which the intermediary imine or enamine is hydrogenated towards the desired amine. The reductive amination reaction of ketones or aldehydes can be done in a gas- or liquid-phase process in the presence of a reducing agent, an amine and if deemed necessary, a suitable catalyst. The reductive amination reaction can be performed in a reaction medium comprising a solvent. In the context of the present invention a solvent is a compound which does not take part in the chemical reaction and which is capable of reducing the concentration in the reaction medium of any of the other compounds, such as reagents, catalysts and reaction products.

As for other hydrogenation reactions, stoichiometric reagents are sometimes used as reducing agents, for example, formic acid or hydrides such as borohydrides or aluminium hydrides. In one embodiment, hydrogen can be used as the reducing agents. Suitable catalysts can be either heterogeneous or homogeneous hydrogenation catalysts. In one embodiment, hydrogenation catalysts can comprise at least one active metal, either in elementary form or in the form of a compound, for example, oxides. Examples of catalysts containing metals in their elementary form are Raney-nickel and Raney-cobalt. In one embodiment, the catalyst comprises a mixture of active metals. The metals can be present in ionic form or as covalently bound. When oxides of the active metals are used, the process can comprise a reduction of the oxide to the elementary metal, typically at higher temperatures, for example, 300° C. to 700° C. (the temperature used in typically determined by the metal and is referred to as "calcining"), and, for example, can be in the presence of hydrogen. Useful hydrogenation catalysts can be selected from one or more of the metals of groups IVb, Vb, VIb, VIIb, VIIIb, Ib or IIb. In one embodiment, catalysts containing nickel, palladium, platinum, cobalt, rhodium, iridium, copper, manganese, tin or ruthenium can be used.

This reaction can be performed either batch wise or continuous. If a continuous installation is used, this can be either a continuous stirred tank reactor (CSTR) or plug flow reactor. The temperature can range from 80 to 300° C. and the pressure from 1 bara to 100 bara. As used herein, "bara" means (Absolute Pressure) Pressure reading relative to absolute vacuum.

The reaction can be performed in an excess of the ketone or aldehyde, in an excess of the amination agent such as dimethylamine or in stoichiometric amounts of the two reagents. The amination reagent may be added in a 10:1 to 1:1 molar ratio based on the enal or aldehyde reactant, or in other embodiments, 5:1 to 1:1, or 4:1 to 1:1, or 4:1 to 2:1, or 3:1 or 4:1 molar ratio, based on the enal or aldehyde reactant.

In one embodiment, the C10 to C12 enal or aldehydes useful in the invention may be reacted with dimethylamine under reductive conditions to obtain alkyl dimethyl amines, or N,N-dimethylalkylamines useful in the invention. In one embodiment, the trialkylamines useful in the invention can be selected from one 4-ethyl-N,N,2-trimethyloctan-1-amine, 4-ethyl, 2-methyl, N,N-dimethylhexan-1-amine, or 2,4-diethyl, N,N-dimethyloctan-1-amine.

In one embodiment, the invention includes a trialkylamine useful in the invention having the formula:

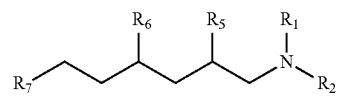

wherein R1 and R2 are each independently selected from straight or branched chain or cyclic hydrocarbon radicals having 1 to 8 carbon atoms;

wherein R5, R6 and R7 are independently at least one of C3H7, C2H5, CH3, or H, or combinations thereof; and wherein R5 and R6 are not H at the same time.

In one embodiment, for the trialkylamine, (a) R1 and R2 can be each independently substituted with groups selected from: —OR3; carboxyl; —NHCOR4; —CONHR4; cyano; —CO$_2$R3; —OCOR3; hydroxy; aryl; heteroaryl; chlorine; or a combination thereof, (b) R3 can be selected from $C_1$-$C_6$ alkyl, substituted $C_1$-$C_6$ alkyl or combinations thereof and (c) R4 can be selected from $C_1$-$C_4$ alkyl or substituted $C_1$-$C_{15}$ alkyl.

In one embodiment, for the trialkylamine, R1 and R2 independently can be CH3; in one embodiment, R1 can be CH3 or C2H5; in one embodiment, R2 can be CH3 or C2H5; in one embodiment, R1 and R2 independently can be C2H5. In one embodiment, for the trialkylamine, R1 can be CH3 when R2 is C2H5, or R1 can be CH2H5 when R2 is CH3.

In one embodiment, for the trialkylamine, R1 can be CH3 or C2H5 and R2 can be a carbohydrate or amino acid.

In one embodiment, for the trialkylamine, R5 and R6 can be C3H7, C2H5, CH3, or combinations thereof; and wherein R7 can be one of C3H7, C2H5, CH3, H or combinations thereof. In one embodiment, for the trialkylamine, R5 can be CH3 or C2H5; in one embodiment, R6 can be CH3 or C2H5; in one embodiment, R5 and R6 independently can be CH3; in one embodiment, R5 and R6 independently can be C2H5. In one embodiment, for the trialkylamine, R5 can be CH3 when R6 is C2H5, or R5 can be CH2H5 when R6 is CH3.

In one embodiment, the trialkylamine can have one to three, or one to two or only two branch points. In one embodiment, the trialkylamine can have one branch point at either the R5 and/or R6 positions. In one embodiment, the trialkylamine can have two branch points which are at the R5 and R6 positions. In one embodiment, the trialkylamine can have three branch points, two of which are at the R5 and R6 positions.

In one embodiment, for the trialkylamine, the number of carbon atoms for the alkyl substituent at the R5 position can be from one to three, or one to two.

In one embodiment, for the trialkylamine, the number of carbon atoms for the alkyl substituent at the R6 position can be from one to three, or one to two.

In one embodiment, the quaternary ammonium compounds of the invention can be made from any of the trialkylamines useful in the invention.

In one embodiment, the invention provides a composition comprising at least quaternary compound derived from at least one trialkylamine of the invention but where the trialkylamine(s) or combination of trialkylamines does not contain any isomeric compound or mixtures, wherein said mixtures contain a number of isomeric compounds, and wherein said isomeric compound(s) can be selected from those of structures:

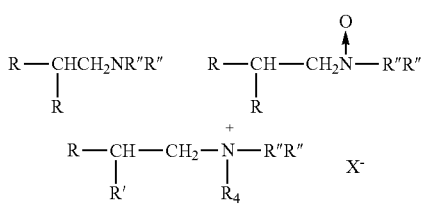

having from 10 to 18 carbon atoms in the R(R')CHCH2- moiety in which R has 5 to 9 carbon atoms, and R' has from 3 to 7 carbon atoms, with most of the compounds having additional methyl or ethyl branches, and in which R' and R" are alkyl or hydroxyalkyl groups or hydrogen and X— is an anion.

In one embodiment, the invention provides a composition comprising at least quaternary compound derived from at least one trialkylamine of the invention but where the trialkylamine(s) or combination of trialkylamines does not contain any isomeric compound or mixture of isomers as described in the previous paragraph, wherein said mixtures contain a number of isomeric compounds, wherein said isomeric compound(s) can be selected from tertiary amines with a higher branched-chain alkyl substituent characterized as having 10 to 18 carbon atoms and an alkyl branch at the 2-position containing 3 to 7 carbon atoms, and additional branching in most of the isomers, with most of the additional branches being methyl groups.

In one embodiment, the invention provides a composition comprising at least quaternary compound derived from at least one trialkylamine of the invention but where the trialkylamine(s) or combination of trialkylamines does not contain any isomers or mixtures of isomers as described in the previous paragraph, wherein said mixtures contain a number of isomeric compounds, and wherein said isomeric compounds can be selected from tertiary amines with a higher branched-chain alkyl substituent characterized as having 12 carbon atoms and an alkyl branch at the 2-position containing 5 carbon atoms or greater, whether or not with additional branching in most of the isomers, whether or not with most of the additional branches are methyl groups and/or ethyl groups.

In one embodiment, the invention provides a composition useful in making the quaternary compound(s) of the invention comprising at least one trialkylamine of the invention which does not contain any trialkylamine or combinations of trialkylamines other than those described herein as being within the scope of this invention.

Trialkylamine intermediates can be further reacted to form a variety of surfactants useful for personal care, home care and industrial applications. Potential surfactants based on a branched trialkylamine hydrophobe include nonionics such as ethoxylated amines; amphoterics such as imidazolines, alkyl betaines and hydroxysultaines and trialkylamine oxides, ethoxylated amine oxides and alkyl diethanolamine oxides; and cationics such as quaternary ammonium salts, bisquaternary ammonium compounds, and ethoxylated quats. Branched trialkylamine-based surfactants can include but are not limited to alkyl betaines, hydroxysultaines, quaternary ammonium salts, and trialkylamine oxides.

In one embodiment, this invention provides at least one quaternary ammonium compound made from any one of the trialkylamines or trialkylamine combinations or compositions of at least trialkylamine of the invention. In another embodiment, this invention provides a process for making any of the quaternary ammonium compound and/or compositions containing at least one quaternary ammonium compound of the invention.

The quats of the invention can be stable toward electrophiles, oxidants, and acids. They can be used alone (or in combination with other surfactants) as disinfectants or disinfecting agents, surfactants, fabric softeners, and as antistatic agents for hair and textiles, e.g. in shampoos and fabric softeners, as well as other products as will be apparent to one of ordinary skill in the art.

In one embodiment, this invention provides at least one quaternary ammonium compound comprising the following formula:

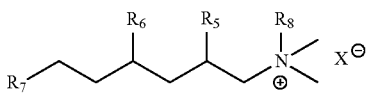

wherein R8 is methyl, ethyl, butyl, or benzyl, and X is a halide or alkosulfate,
wherein R5, R6 and R7 are independently at least one of C3H7, C2H5, CH3, or H; and
wherein R5 and R6 are not H at the same time.

In one embodiment, this invention provides at least one quaternary ammonium compound of the invention comprising the formula:

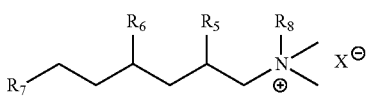

wherein R5 and R6 are C3H7, C2H5, CH3, or combinations thereof; and
wherein R7 is one of C3H7, C2H5, CH3, H or combinations thereof.

In one embodiment, for the quaternary ammonium compounds, R5 can be CH3 or C2H5; in one embodiment, R6 can be CH3 or C2H5; in one embodiment, R5 and R6 independently can be CH3; in one embodiment, R5 and R6 independently can be C2H5. In one embodiment, for the quaternary ammonium compound, R5 can be CH3 when R6 is C2H5, or R5 can be CH2H5 when R6 is CH3; R8 can be benzyl or butyl; X— can be halide, for example, chloride, bromide or iodide; in one embodiment, the quaternary ammonium compound can be selected from N-benzyl-2,4-diethyl-N,N-dimethyloctan-1-aminium chloride or N-butyl-2,4-diethyl-N,N-dimethyloctan-1-aminium bromide.

In one embodiment, this invention includes a composition comprising at least one quaternary ammonium compound or multiple quaternary ammonium compounds of the invention which composition does not contain any quaternary ammonium compounds other than those of the invention.

In one embodiment, the composition containing the quaternary compound of the invention can comprise at least one nonionic surfactant, anionic surfactant, cationic surfactant, amphoteric surfactant, or combinations thereof.

In one embodiment, a composition of the invention can comprise 0.01% to 30% by weight of said quaternary ammonium compound based on the total weight of the composition equaling 100 weight %.

In one embodiment, the invention provides at least one quaternary ammonium compound of the invention or composition(s) comprising said quaternary ammonium compound which is a disinfecting agent.

In one embodiment, the invention provides at least one quaternary ammonium compound (for example, N-benzyl-2,4-diethyl-N,N-dimethyloctan-1-aminium chloride) having a minimum lethal concentration against at least one microbe selected from gram-positive bacteria, gram-negative bacteria, and/or yeast, when used at concentrations of less than 200 ppm, or less than 150 ppm, less than 100 ppm, or less than 75 ppm, or less than 65 ppm.

In one embodiment, the invention provides at least one quaternary ammonium compound of the invention (for example, N-benzyl-2,4-diethyl-N,N-dimethyloctan-1-aminium chloride) having a minimum lethal concentration against *E. coli, S. aureus* and/or *C-albicans* when used at concentrations of less than 200 ppm, or less than 150 ppm, less than 100 ppm, or less than 75 ppm, or less than 65 ppm.

In one embodiment, the invention provides at least one quaternary ammonium compound of the invention (for example, N-benzyl-2,4-diethyl-N,N-dimethyloctan-1-aminium chloride) having a minimum lethal concentration against *E. coli, S. aureus* and/or *C-albicans* when used at concentrations of less than 200 ppm, or less than 150 ppm, less than 100 ppm, or less than 75 ppm where the quaternary ammonium compound is N-benzyl-2,4-diethyl-N,N-dimethyloctan-1-aminium chloride.

As described herein, when the alkylating agent used to make the quaternary ammonium comound is benzyl chloride, the resulting product is a benzalkonium chloride, which can have antimicrobial properties.

Benzalkonium chloride (BAC) is a cationic quaternary ammonium salt (quat) with demonstrated antimicrobial activity. BACs with C8 to C18 alkyl chain lengths are used as biocides in wood treatment, aqueous processes and as preservatives in water-based formulations. BACs are made from the corresponding alkyl dimethylamines by reaction with benzyl chloride. The alkyl component of the USP-grade BAC biocide and preservative is composed of a blend of alkyl chains with a well-defined C12 to C18 chain distribution based on fractionated coconut or palm kernel fatty acids. Other grades of BAC are also available with a more loosely defined alkyl chain distribution, or with a single alkyl chain length. With pressure to replace triclosan, BAC has become a leading active ingredient in antimicrobial hand wash. Benzalkonium chlorides or blends are also the active ingredient in many antimicrobial surface cleaners, including wipes The quaternary ammonium compounds useful in the invention can also function as a phase transfer catalyst (PTC), In one embodiment, the invention provides at least one process for using at least one quaternary ammonium compound of the invention.

In one embodiment, the invention provides at least one process for using at least one quaternary ammonium compound of the invention as a phase transfer catalyst. In one embodiment, the invention provides at least one process wherein the quaternary ammonium compound is used as phase transfer catalyst in a process for making a enal or aldehyde, whether branched or not, for example, any enal or aldehyde useful in making any product of this invention, for example, products including but not limited to trialkylamines (including branched or non-branched trialkylamines), amino acids, sarcosine product, glucamine products, trialkylamine oxides, quaternary ammonium compounds, carboxybetaines, and/or hydroxysultaines of the invention.

The invention also includes processes of making quaternary ammonium compounds of the invention. Any trialkylamines useful in the invention or combinations thereof can be reacted with alkylating agents such as halides (e.g. methyl chloride) or alkyl sulfates (e.g. dimethyl sulfate) to form the cationic quaternary ammonium salts ("quats") of the invention. The branched C10-12 N,N-dimethylalkylamines useful in the invention can be reacted to form branched C10-C12 quaternary ammonium compounds of the invention. For example, branched BAC-b12 (N-benzyl-2,4-diethyl-N,N-dimethyloctan-1-aminium chloride) and N-butyl-2,4-diethyl-N,N-dimethyloctan-1-aminium bromide (branched C12-butyl quat.) are examples of branched C10-C12 quaternary ammonium compounds of the invention.

In one embodiment, this invention provides at least one quaternary ammonium compound of the invention wherein the alkylating agent selected to make the quaternary ammonium compound can be selected from at least one of C1-C4 alkyl chloride, C1-C4 alkyl bromide or C1-C4 alkyl iodide, benzyl chloride, benzyl bromide or benzyl iodide, or combinations thereof.

In one embodiment, this invention provides at least one quaternary ammonium compound of the invention wherein the alkylating agent can be selected from at least one of methyl chloride, ethyl chloride, propyl chloride, butyl chloride, methyl bromide, ethyl bromide, propyl bromide, butyl bromide, benzyl chloride, benzyl bromide or combinations thereof. In one embodiment, the alkylating agent can be C1-C4 alkyl bromide.

In one embodiment, the alkylating agent can be the quaternary ammonium compound of the invention wherein the alkyl bromide is butyl bromide or any isomers thereof.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

This invention can be further illustrated by the following examples of preferred embodiments thereof, although it will be understood that these examples are included merely for purposes of illustration and are not intended to limit the scope of the invention unless otherwise specifically indicated.

EXAMPLES

For the Examples herein, some of the abbreviations used herein are defined in the following Table and others are throughout the Description and the Examples:

| Abbreviation | Name |
| --- | --- |
| BAC | Benzalkonium chloride |
| CSTR | Continuous stirred tank reactor (CSTR) |
| ELSD | Evaporative light scattering detector |
| EtOH | Ethanol |
| GC-FID | Gas Chromatography-Flame ionization detector |
| HEH | 2-Ethylhexanal |
| nHBu | n-Butyraldehyde |
| (TBABr) | Tetrabutyl ammonium bromide |
| Wt | Weight |

Example 1. Synthesis of C11 Enal
(4-ethyl-2-methyloct-2-enal)

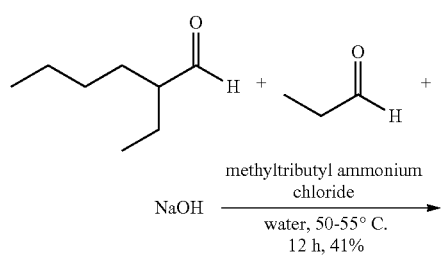

-continued

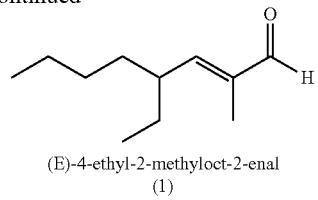

(E)-4-ethyl-2-methyloct-2-enal
(1)

To a solution of NaOH (250 g, 3.12 mol) in water (303 mL) was added tributylmethylammonium chloride (49 g, 0.156 mol). To this solution, a premix solution of 2-ethyl hexaldehyde (500 g, 3.90 mol) and propionaldehyde (190 g, 3.28 mol) was added dropwise over the period of 5 h. The addition was maintained such that the temperature of the reaction did not exceed 55° C. The contents of the reaction were stirred at 50° C. for 12 h. The reaction was cooled to room temperature and the contents were transferred to a separatory funnel. The aqueous layer was separated and the organic layer was washed sequentially with water (500 mL), saturated aq. NH$_4$Cl (500 mL) and water (500 mL). The organic layer was separated, dried over MgSO$_4$ and filtered. The pure enal of this Example was distilled at 85° C. (vapour temperature) under 4 mm reduced pressure.

Example 2. Reduction of C11 enal
4-ethyl-2-methyloctanal (C11-Aldehyde)

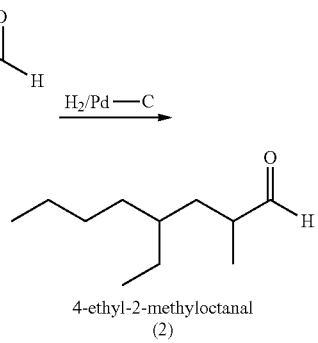

4-ethyl-2-methyloctanal
(2)

The C11-enal obtained in Example 1 was hydrogenated using palladium (Pd)—C (1 mol %) under hydrogen pressure (400 psi) at 120° C. The resultant aldehyde in this Example 2, 4-ethyl-2-methyloctanal, was distilled at 80° C.-85° C. (vapor temperature) under 3 mm reduced pressure.

Example 3: Synthesis of 2,4-diethyl-2-octenal

Charge a 3 neck, 1 L (liter) flask with Water (133 ml), sodium hydroxide (56.7 g, 1418 mmol), and tetrabutylammonium chloride (25.0 g, 90 mmol). Using a magnetic stir bar, stir to dissolve. Attach a 500 mL liquid dropping funnel charged with butyraldehyde (75.1 g, 1042 mmol) and 2-ethylhexanal (257.2 g, 2006 mmol). Add the aldehyde mixture to the aqueous mixture in the pot dropwise over 2-3 h. After aldehyde addition is complete, pour the mixture into a 1 L separatory funnel. Separate the aqueous layer and wash the organic layer with brine (1×100 mL) and water (2×100 mL). Separate the organic layer, dry over MgSO4, and filter. The crude reaction mixture (190 g) contains 46% 2-ethylhexanal and 33% 2,4-diethyloct-2-enal. This corresponds to 100% conversion of n-butyraldehyde and 56.9% yield, based on moles of butyraldehyde, of 2,4-diethyloctenal.

Example 4: Synthesis of 2,4-diethyl-2-octenal

Charge a 3 neck, 12 L flack with Water (1596 ml), sodium hydroxide (680.4 g), and tetrabutylammonium bromide (348.12 g). Using a magnetic stir bar, stir to dissolve. Attach 1 L liquid dropping funnel charged with butyraldehyde (901.2 g) and 2-ethylhexanal (3086.4 g). Add the aldehyde mixture to the aqueous mixture dropwise over 2 to 3 h. After aldehyde addition is complete, pour the mixture into a separatory funnel. Separate the aqueous layer and wash the organic layer with brine (300 ml) and water (600 ml). Separate the aqueous layer and wash the organic layer with 5% HCl (200 ml) and water (100 ml). Separate the organic layer, dry over MgSO4, filter, and analyze by gas chromatography. Crude reaction mixture (2278 g) contains 44% 2-ethylhexanal, 1% 2-ethyl-hex-2-enal, 1% 2-ethylhexanol, 2% 2-ethylhexanoic acid, 44% 2,4-diethyl-octenal, and the balance unidentified heavies. This corresponds to 60% yield of 2,4-diethyloctenal.

Example 5: Synthesis of 2,4-diethyl-2-octenal with Benzalkonium Chloride as the Phase Transfer Catalyst (PTC)

Charge a 3 neck, 1 L flask with Water (75 ml), sodium hydroxide (28.3 g, 708 mmol), and benzalkonium chloride (8.84 g, 26 mmol). Using a magnetic stir bar, stir to dissolve. Attach 1 L liquid dropping funnel charged with butyraldehyde (37.5 g, 520 mmol) and 2-ethylhexanal (133.4 g, 1040 mmol). Add the aldehyde mixture to the aqueous mixture dropwise over 2 to 3 h. After aldehyde addition is complete, drain mixture by parts into a 3 L separatory funnel. Separate the aqueous layer and wash the organic layer with brine (50 ml) and water (100 ml). Separate the aqueous layer and wash the organic layer with 5% HCl (50 ml) and water (100 ml). Separate the organic layer, dry over MgSO4, filter, and analzye by gas chromatography. Crude reaction mixture (167.03 g) contains 60% 2-ethylhexanal, 5.5% 2-ethyl-hex-2-enal, 0.5% 2-ethylhexanol, 1.5% 2-ethylhexanoic acid, 17% 2,4-diethyl-octenal, and the balance unidentified heavies. This corresponds to 30% yield of 2,4-diethyl-2-octenal.

Example 6: Synthesis of 2,4-diethyl-2-octenal without PTC

Charge a 3 neck, 1 L flask with water (133 ml), sodium hydroxide (56.7 g, 1418 mmol). Using a magnetic stir bar, stir to dissolve. Attach a 500 mL liquid dropping funnel charged with butyraldehyde (75.1 g, 1042 mmol) and 2-ethylhexanal (257.2 g, 2006 mmol). Add the aldehyde mixture to the aqueous mixture in the pot dropwise over 2-3 h if possible. After aldehyde addition is complete, pour the mixture into a 1 L separatory funnel. Separate the aqueous layer and wash the organic layer with brine (1×100 mL) and water (2×100 mL). Separate the organic layer, dry over MgSO4, filter, and analyze by gas chromatography. Crude reaction mixture contains 75% 2-ethylhexanal, 6.2% 2-ethyl-hex-2-enal, 2.7% 2,4-diethyloct-2-enal, and the balance being unidentified materials with a boiling point higher than that of 2,4-diethyloct-2-enal (heavies). Yield is 3.2%.

Examples 7-12: Synthesis of 2,4-diethyl-2-octenal with varying PTC

These examples were carried out as described in Example 3 except the concentration of tetrabutyl ammonium bromide (TBABr) was varied relative to n-butyraldehyde (nHBu) as indicated in Table 1. 2HEH=2-ethylhexanal; C12=2,4-diethyloctenal

TABLE 1

| Example Number | TBABr:nHBu | NaOH:nHBu | 2HEH:nHBu | C12 Yield |
|---|---|---|---|---|
| 7 | 0.09 | 1.4 | 2.0 | 60% |
| 8 | 0.07 | 1.4 | 2.0 | 60% |
| 9 | 0.05 | 1.4 | 2.0 | 60% |
| 10 | 0.04 | 1.4 | 2.0 | 40% |
| 11 | 0.03 | 1.4 | 2.0 | 20% |
| 12 | 0.02 | 1.4 | 2.0 | 38% |

Examples 13-16: Synthesis of 2,4-diethyl-2-octenal with Varying NaOH Equivalents These examples were carried out according to the procedure outlined in Examples 13-16 except the equivalents of NaOH relative to n-butyraldehyde (nHBu) were varied as shown in Table 2. The data in Table 2 demonstrates that using a ratio of 1.15 to 1.25 of NaOH:nHbu provides a enal yield of at least 40%.

TABLE 2

| Example Number | Mmol nHBu | Mmol NaOH | NaOH:nHBu | C12 Yield |
|---|---|---|---|---|
| 13 | 520 | 650 | 1.25 | 41% |
| 14 | 520 | 598 | 1.15 | 42% |
| 15 | 520 | 520 | 1.00 | 33% |
| 16 | 520 | 260 | 0.5 | 28% |

Examples 17-24: Continuous Synthesis of 2,4-diethyl-2-octenal

A jacketed 3 L glass round bottom with four necks and a bottom drain containing a stop cock, was used as a continuous stirred tank reactor. The center neck was fitted with an overhead stirrer controlled by an electric motor. The left neck was fitted with a Claisen tube to which are connected two veritcally mounted 2 L glass feed tanks. Each feed tank was attached to a 0-20 mL Eldex brand liquid feed pump. The drain was connected to the intake of a high speed circulating pump. The discharge of the pump passes through an inline static mixer and returns to the CSTR through the right neck. A slip stream of product was removed on the downstream side of the static mixer through a 0-40 mL Eldex pump and into another vertically mounted 2 L glass tank that serves as a decanter. The fourth neck of the CSTR contains a J-type thermocouple connected to a JKEM type temperature indicator. Heating was provided by a circulating bath containing a 50/50 mixture of water and ethylene glycol. The heating medium was circulated through the glass jacket on the reactor to keep the reactor mixture at the desired temperature.

In a typical aldol experiment, one glass feed tank was filled with a 20% solution of NaOH and the other feed tank was filled with a mixture of 60% HEH, 35% nHBu, and 5% BAC. The reactor was charged with 1500 mL of a 2:1 mixture of crude material and NaOH solution. The contents were stirred at 250 rpm and heated to 55° C. The circulating pump was started and material was moved through the static mixer and returned to the CSTR. When the target temperature was reached, the organic feed pump was begun at 15.0 mL/min and the caustic feed pump was begun at 6.0 mL/min. The product takeoff pump was begun at 21.0 mL/min. Under these conditions, the residence time in the reactor was approximately 60 minutes. One hour after startup the product decanter was emptied and this material discarded. After this time, samples were collected every hour. The bottom aqueous material was decanted from the product tank and weighed. The upper organic layer was decanted, weighed, and analyzed by gas chromatography. The crude organic was retained for distillation. After 7 hours, the experiment was discontinued. In this way, approximately 3 L of crude organic was obtained daily.

Distillation of the decanted, crude organic material was conducted on a 2" glass Oldershaw column. The column stands 10 feet tall and was approximately 24 trays. The column is attached to a 3 L three neck glass round bottom at the bottom and an overhead chilled glycol condenser. The top tray of the column was topped by a "swinging gate" style takeoff controller with a reflux control magnet attached to an electric timer. The disillate from the swinging gate passes through a second glycol chilled condenser before collecting in a glass fraction cutter. The entire column was maintained under 100 torr vacuum by a Welch type vacuum pump. A similar 1" Oldershaw column was used employing 30 glass trays. Material was fed constantly into the column from a 4 L glass feed tank. The feed rate was controlled by a bellows type pump and passed through a pre-heater set to 120° C. The basepot overflow was removed through a glass sample thief attached to a glycol chilled condenser. A stainless steel solenoid valve and stainless steel needle valve were used to control the rate of overflow. The solenoid was controlled by an electric timer and the overflow product tank was held at 15 torr.

Organic samples were studied by gas chromatography on an Agilent 6890N. The aqueous samples were run on a Restek RTX-1 fused silica catalog #10126 column (length 60 m, diameter 250 um, film 0.25 um) analyzed by a flame ionization detector (GC-FID). The configuration settings were as follows. Heat the oven to 50° C. initially and hold for 3 minutes, ramp the temperature to 125° C. at 12° C./minute, and hold there for 3 minutes. Next, increase the temperature up 7° C./min to a temperature of 165° C. Then, increase the temperature up 15° C./min to a final temperature of 240° C. The detector setting was held at 300° C. Table 3 shows the yield of C12 enal obtained from a continuous process, changing the ratio of reactants, PTC loading, residence time and temperature.

TABLE 3

3 L CSTR results at 2:1 HEH:nHBu ethyl-hex-2-enal

| Example Number | OH:C4 | PTC:C4 | Residence Time (min) | Temperature (° C.) | Butyraldehyde Conversion | C12 Yield (Based on mols of butyraldehyde fed) |
|---|---|---|---|---|---|---|
| 17 | 1.41 | 0.05 | 60 | 53.1 | 97.4% | 50.1% |
| 18 | 1.46 | 0.05 | 110 | 54.2 | 93.1% | 60.8% |
| 19 | 1.49 | 0.05 | 110 | 62.6 | 93.2% | 57.6% |
| 20 | 1.23 | 0.05 | 60 | 57.1 | 84.5% | 43.6% |
| 21 | 1.10 | 0.05 | 60 | 56.9 | 88.6% | 50.1% |
| 22 | 1.04 | 0.05 | 60 | 56.9 | 89.3% | 55.8% |
| 23 | 1.17 | 0.03 | 60 | 55.0 | 87.9% | 41.2% |
| 24 | 1.51 | 0.05 | 60 | 70.5 | 98.6% | 51.9% |

Example 25: Hydrogenation of 2,4-diethyl-2-octenal

A 2 L Hastelloy Autoclave Engineers autoclave is charged with 400 g of purified 2,4-diethyl-2-octenal and 400 g of dry isopropanol. 10.0 g of 0.75% Pd on Al2O3 support is added to a steel mesh catalyst basket. The basket is attached to the stirring shaft of the autoclave above the impeller. The autoclave is sealed and purged with hydrogen gas. The autoclave is brought to 345 kPa with $H_2$ and heated to 150° C. The autoclave is then brought 6895 kPa with $H_2$. Using a gas reservoir system, the autoclave pressure is maintained for 6 h. After 6 h, the autoclave is cooled and vented. The reaction consumed 5.4 Gmol of hydrogen. The crude reaction mixture (782 g) contains 50% isopropanol, 45% 2,4-diethyloctanal, 2.37% 2,4-diethyloctenal, 7.7% 2,4-diethyloctanol, and 3.5% 2,4-diethyl-oct-2-en-1-ol. This corresponds to 98% conversion and 77% yield of 2,4-diethyloctenal.

Examples 26-28: Hydrogenation of 2,4-diethyl-2-octenal

Synthesis of 2,4-diethyl-2-octanal was carried out in the same manner as Example 25 above except the hydrogen pressure was varied as indicated in Table 4.

TABLE 4

| Example Number | Pressure (kPa) | Enal Conversion | 2,4-diethyloctanal Yield |
|---|---|---|---|
| 26 | 6895 | 98% | 77% |
| 27 | 5171 | 66% | 54% |
| 28 | 3447 | 60% | 55% |

Examples 29-32: Catalyst Comparison

A series of catalysts of differing Pd loading and supports, obtained from Evonik Corporation, were tested in the following manner: A 300 mL stainless steel Autoclave Engineers autoclave is charged with 50 g of purified 2,4-diethyl-2-octenal and 50 g of dry isopropanol. 5.0 g of catalyst obtained from Evonik is added to a steel mesh catalyst basket. The basket is attached to the stirring shaft of the autoclave above the impeller. The autoclave is sealed and purged with hydrogen gas. The autoclave is brought to 345 kPa with H2 and heated to 150° C. The autoclave is then brought 6895 kPa with H2. Using a gas reservoir system, the autoclave pressure is maintained for 4 h. After 4 h, the autoclave is cooled and vented. The results are presented in Table 5.

TABLE 5

| Example Number | Catalyst | Pd Loading | Support | Conversion | Yield |
|---|---|---|---|---|---|
| 29 | Noblyst 1512 | 0.7% | Carbon | 92% | 80% |
| 30 | Noblyst 1006 | 1.0% | Carbon | 91% | 80% |
| 31 | Noblyst 1005 | 2.0% | Silica | 44% | 33% |
| 32 | E 105 O/W | 5.0% | Carbon | 62% | 42% |

Example 33: Hydrogenation of 2,4-diethyl-2-octenal with Ru

A 300 mL stainless steel Autoclave Engineers autoclave is charged with 50 g of purified 2,4-diethyl-2-octenal and 50 g of dry isopropanol. 5.0 g of 3% Run on 2 mm carbon extract support obtained from Johnson-Matthey is added to a steel mesh catalyst basket. The basket is attached to the stirring shaft of the autoclave above the impeller. The autoclave is sealed and purged with hydrogen gas. The autoclave is brought to 345 kPa with H2 and heated to 150° C. The autoclave is then brought 6895 kPa with H2. Using a gas reservoir system, the autoclave pressure is maintained for 4 h. After 4 h, the autoclave is cooled and vented. The reaction consumed 0.8 Gmol of hydrogen. The crude reaction mixture (85 g) contains 30% isopropanol, 12% 2-ethylhexanol, 3.4% 2,4-diethyloctanal, 14% 2,4-diethyloctenal, 18% 2,4-diethyloctanol, and 21% 2,4-diethyl-oct-2-en-1-ol. This corresponds to 76% conversion and 7% yield of 2,4-diethyloctenal Example 34: Biodegradability—OECD 301B The biodegradability of the branched aldehyde intermediates of Example 2 (4-ethyl-2-methyloctanal) and Example 25 (2,4-diethyl-2-octenal) were determined by the Ready Biodegradability—CO2 Evolution Test—Degradation of test compound according to OECD Guidelines for Testing of Chemicals $CO_2$ Evolution Test 301B.

TABLE 6

| | Biodegradation (%) | | |
|---|---|---|---|
| Days | sodium acetate control | C11 aldehyde Example 2 | C12 aldehyde Example 25 |
| 0 | 0 | 0 | 0 |
| 2 | 32 | 0 | 0 |
| 6 | 52 | 15 | 0 |
| 7 | 54 | 21 | 9 |
| 9 | 60 | 31 | 27 |
| 14 | 66 | 47 | 48 |
| 19 | 69 | 54 | 53 |
| 23 | 71 | 56 | 53 |
| 28 | 72 | 57 | 55 |
| 29 | 74 | 57 | 55 |
| 29 | 78 | 61 | 57 |

Example 35. Conversion of C11 Aldehyde to 4-ethyl-N,N,2-trimethyloctan-1-amine (3) (C11-amine)

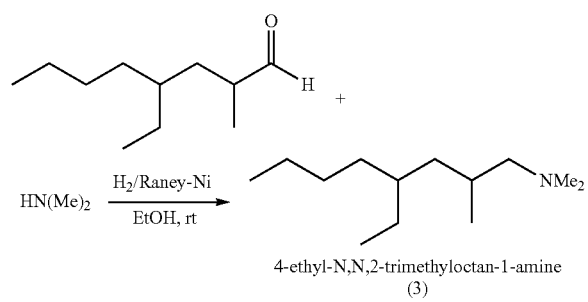

To a 500 mL thick-walled parr-shaker flask, Raney-Ni (2 g) was added. A solution of dimethylamine (11% solution in EtOH, 193 g, 470 mmol) was added to this flask. To this solution was then added $C_{11}$-aldehyde (2) (20 g, 117 mmol) obtained in the last step and the contents were hydrogenated using $H_2$ gas (30 psi) for 12 h. After the reaction was complete, the catalyst was filtered and the volatiles were evaporated under reduced pressure. The residue was diluted with EtOAc (200 mL) and 10% aq. HCl (200 mL). The organic layer was separated and the product aq. Layer was washed with additional EtOAc (200 mL). The aq. Layer was separated and basified using saturated aq. $NaHCO_3$ solution. This solution was then transferred to a separatory funnel and the pure product extracted using EtOAc (3×300 mL). The organic layer was separated, dried over MgSO4 and concentrated under reduced pressure to afford the pure C11 amine (3).

Example 36: Synthesis of 4-ethyl, 2-methyl, N,N-dimethylhexan-1-amine Via 4-ethyl, 2-methyloctanal

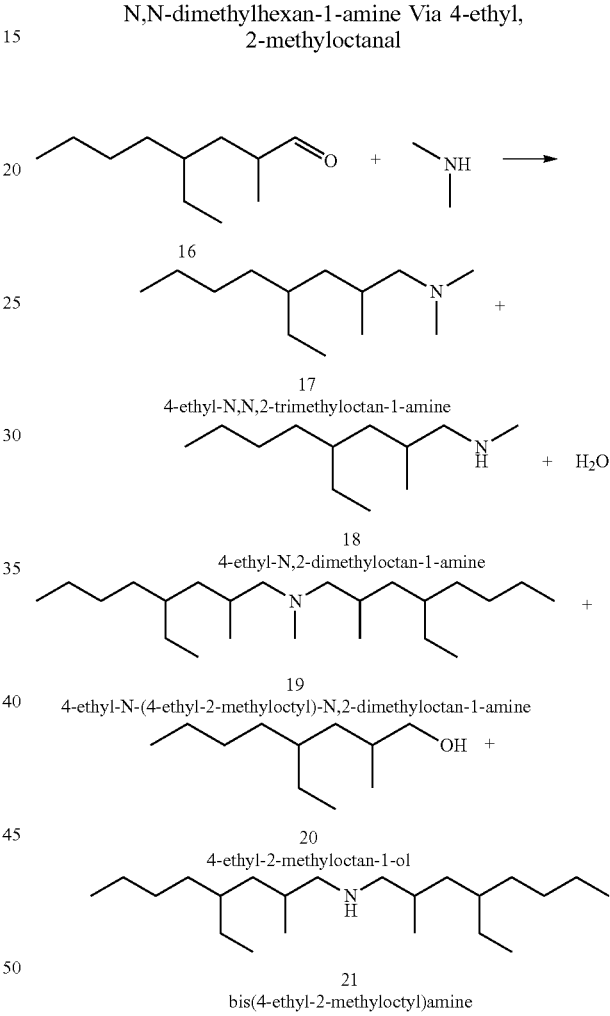

A vertical fixed bed reactor was charged with 50 ml (50 g) of a tableted $CuO/ZnO/Al_2O_3$ catalyst. After activation with hydrogen (180° C., ambient pressure, 24 h) a continuous gaseous flow was fed to the reactor which consist of hydrogen, dimethylamine and 4-ethyl, 2-methyloctanal (16) in the reactor at a pressure of 10 barg and a temperature of 250° C. The ratio of dimethylamine to the aldehyde to hydrogen was set at 3/1/50 and the aldehyde feed was set at 0.15 g/g catalyst/h. Bypass high pressure samples were taken from the reaction mixture downstream of the reactor and analyzed by gas chromatography. The experiments were run for 100 h and at steady state, the conversion was 99.9% and the yield towards the wanted 4-ethyl, 2-methyl, N,N-dimethylhexan-1-amine (17) was 85.04%. Yields of the different side-products (4-ethyl, 2-methylhexanol (20); 4-ethyl, 4-ethyl,2-methyl, N-methylhexan-1-amine (18); N-(4-ethyl, 2-methyl hexyl)-N-methylhexan-1-amine (19) and bis (4-ethyl, 2-ethyl hexyl)amine) were respectively 0.36%, 8.15%, 1.63% and 0.18%.

Example 37: Synthesis of 2,4-diethyl, N,N-dimethyloctan-1-amine via 2,4-diethyl-2-octenal

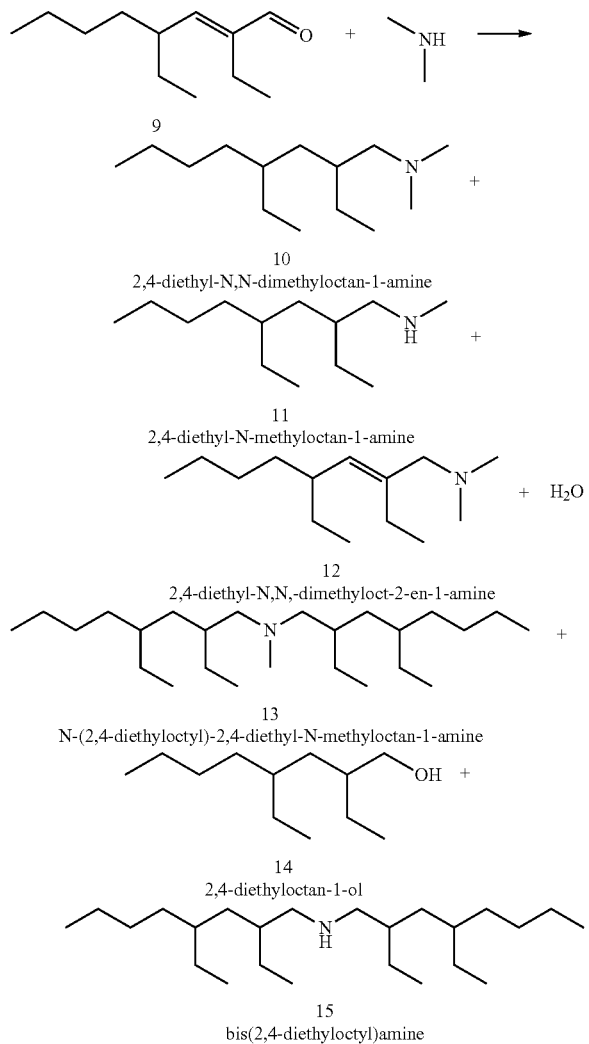

A vertical fixed bed reactor was charged with 50 ml (50 g) of a tabletted CuO/ZnO/Al catalyst. After activation with hydrogen (180° C., ambient pressure, 24 h) a continuous gaseous flow was fed to the reactor which consist of hydrogen, dimethylamine and 2,4-diethyl-2-octenal (9) in the reactor at a pressure of 10 barg and a temperature of 250° C. The ratio of dimethylamine to the aldehyde to hydrogen was set at 3/1/50 and the aldehyde feed was set at 0.15 g aldehyde/g catalyst/hour. Bypass high pressure samples were taken from the reaction mixture downstream of the reactor and analyzed by gas chromatography. The experiments were run for 100 h and at steady state, the conversion was 99.9% and the yield towards the desired 2,4-diethyl, N,N-dimethyloctan-1-amine was 71.5%. Yields of the different side products 2,4-diethyloctanol; 2,4-diethyl, N-methyloctan-1-amine; 2,4-diethyl,N,N-dimethyloct-2-en-1-amine; N-(2,4-diethyloctyl)-N-methyloctan-1-amine and bis (2,4-diethyloctyl)amine) were respectively 2.13%, 5.20%, 11.14%, 3.20% and 1.25%.

Example 38: Synthesis of Branched BAC-b12 (N-benzyl-2,4-diethyl-N,N-dimethyloctan-1-aminium Chloride 2,4-Diethyl N,N-dimethyloctylamine (3.00 g; 14.06 mmol) and benzyl chloride (1.78 g; 14.06 mmol; 1.0 equiv) were combined in a 40 mL vial with a magnetic stir bar, which was heated with stirring in a 77° C. heat block for 6 h, at which point the mixture had solidified. Water (1.59 g) was added, and the mixture was stirred with heating at 77° C. for an additional 6 h to afford 99.3% conversion of the amine to branched BAC-b12 according to HPLC analysis. The resulting mixture is ca. 75% branched BAC-12 in water as a homogeneous liquid.

1H NMR (DMSO-d6): δ7.7-7.4 (m, 5H); 4.65 (m, 2H); 3.44 (m), 1H); 3.15 (t, J=11.7 Hz); 3.0-2.9 (m, 6H); 1.55-1.05 (m, 14H); 0.95-0.7 (m, 9H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection detection): tR 3.6 min. (starting amine); 4.1 min (branched BAC-b12).

Example 39: Antimicrobial Screening of BAC-b12

The minimum inhibitory concentration (MIC) and the minimum lethal concentration (MLC) of the chemicals were determined using a microplate dilution assay. Quats were provided as aqueous solutions, while Triclosan and Chloroxylenol were provide as powders which were first dissolved at 5 weight percent in absolute ethanol. A two-fold serial dilution series of each test chemical was prepared in Trypticase Soy Broth at 20% of the standard concentration (TSB20) and in Sabouraud Dextrose Broth at 20% of the standard concentration (SDB20) in 96-well micro-titer plates. A total of 10 dilutions were prepared and four replicate tests were performed for each dilution. The high concentration preparations of Triclosan and Chloroxylenol showed undissolved suspended material, but the suspensions were stable enough to prepare the dilutions series. Control solutions containing only media were included for each plate. Suspensions of Staphylococcus aureus, Escherichia coli, and Candida albicans were prepared from one-day old agar plate cultures in Butterfields Phosphate Diluent to a concentration of approximately $10^7$ to $10^8$ cells per milliliter. Each test well was inoculated with the diluted culture suspensions at a concentration of $10^3$ to $10^4$ cells per well and then incubated at 32° C. with shaking at 150 rpm for approximately 24 hours, after which the optical density of each well was determined spectrophotometrically at 600 nm. Wells containing uninoculated media without test chemical were included in each plate as negative controls and, following inoculation, as positive controls. MIC values were determined as the lowest concentration of test chemical for which all four replicates showed less than 10% (MIC<10%) or 50% (MIC<50%) of the positive control optical density.

Selected wells at or below the MIC were tested for MLC by spotting three microliters from each replicate well onto Trypticase Soy agar for S. aureus and E. coli, or Sabouraud Dextrose agar for C. albicans. The MLC was determined as the lowest concentration of test chemical for which at least three of the four replicates showed absence of growth on the agar.

The results are shown in Table 7.

TABLE 7

Antimicrobial effectiveness of BACs with different alkyl chain length and distribution. BAC = benzalkonium chloride, C8-18; BAC50 = benzalkonium chloride, C12-18; BAC-12 linear = benzalkonium chloride, C12; BAC-b12 = N-benzyl-2,4-diethyl-N,N-dimethyloctan-1-aminium chloride

| | | | Weight percent | | |
|---|---|---|---|---|---|
| Type | Organism | Compound | MIC < 10% | MIC < 50% | MLC |
| Gram neg bacteria | *Escherichia coli* | BAC (Sigma) | 0.00020 | 0.00020 | 0.00078 |
| | | BAC50 (Thor) | 0.00039 | 0.00039 | 0.00078 |
| | | BAC-12 linear | 0.00078 | 0.00078 | 0.00078 |
| | | BAC-b12 branched | 0.0063 | 0.0063 | 0.0063 |
| | | Chloroxylenol | >0.0083 | >0.0083 | >0.0083 |
| | | Triclosan | 0.00010 | 0.00010 | 0.00010 |
| Gram pos bacteria | *Staphylococcus aureus* | BAC (Sigma) | 0.00020 | 0.00020 | 0.00020 |
| | | BAC50 (Thor) | 0.00020 | 0.00020 | 0.00020 |
| | | BAC-12 linear | 0.00020 | 0.00020 | 0.00020 |
| | | BAC-b12 branched | 0.00039 | 0.00039 | 0.00078 |
| | | Chloroxylenol | 0.0042 | 0.0042 | >0.0083 |
| | | Triclosan | 0.00002 | 0.00002 | 0.00003 |
| Yeast | *Candida albicans* | BAC (Sigma) | 0.00078 | 0.00078 | 0.00078 |
| | | BAC50 (Thor) | 0.00078 | 0.00078 | 0.00078 |
| | | BAC-12 linear | 0.0016 | 0.00078 | 0.0016 |
| | | BAC-b12 branched | 0.0063 | 0.0063 | 0.0063 |
| | | Chloroxylenol | 0.0083 | 0.0083 | >0.0083 |
| | | Triclosan | 0.0016 | 0.0016 | >0.0016 |

(MIC = minimum inhibitory concentration; MIC < 10% and MIC < 50% are the lowest concentrations of test compound showing consistent reduction in growth to less than 10% and less than 50% of control level, respectively.
MLC = minimum lethal concentration as judged by absence of any surviving cells following treatment.)
(MIC = minimum inhibitory concentration; MIC < 10% and MIC < 50% are the lowest concentrations of test compound showing consistent reduction in growth to less than 10% and less than 50% of control level, respectively.
MLC = minimum lethal concentration as judged by absence of any surviving cells following treatment.)

Example 40: Synthesis of Branched C12 Enal with (Branched BAC as PTC)

A 100 mL three neck round bottom flask is charged with 7.77 g (194 mmol) of NaOH pellets. 30 mL of water is added and the mixture stirred by means of a magnetic stir bar until the NaOH is dissolved. 3.14 g of a 75 weight % aqueous solution of N-benzyl-2,4-diethyl-N,N-dimethyloctan-1-aminium chloride is added and stirring continues. A 50 mL dropping funnel, glycol chilled condenser, and thermometer are attached to the round bottom. The entire apparatus is brought to 50° C. The dropping funnel is charged with a mixture of n-butyraldehyde (10 g, 139 mmol) and 2-ethylhexanal (35.6 g, 277 mmol) and the aldehyde mixture is added slowly dropwise to the caustic mixture. After three hours, the mixture is cooled and poured into a 125 mL separatory funnel. The bottom aqueous layer is separated. The upper organic phase is washed with water and brine. The organic layer is dried over MgSO4, filtered, and the filtrate analyzed by GC. GC analysis shows 51% yield of 2,4-diethyl-oct-2-enal.

Example 41: Synthesis of Branched C12 Enal with (Branched BAC as PTC)

A 100 mL three neck round bottom flask is charged with 7.77 g (194 mmol) of NaOH pellets. 30 mL of water is added and the mixture stirred by means of a magnetic stir bar until the NaOH is dissolved. 3.14 g of a 75 weight % aqueous solution of N-benzyl-2,4-diethyl-N,N-dimethyloctan-1-aminium chloride is added and stirring continues. 2-ethylhexanal (35.6 g, 277 mmol) is added. A 50 mL dropping funnel, glycol chilled condenser, and thermometer are attached to the round bottom. The entire apparatus is brought to 50° C. The dropping funnel is charged with of n-butyraldehyde (10 g, 139 mmol) and the aldehyde mixture is added slowly dropwise to the caustic mixture. After three hours, the mixture is cooled and poured into a 125 mL separatory funnel. The bottom aqueous layer is separated. The upper organic phase is washed with water and brine. The organic layer is dried over $MgSO_4$, filtered, and the filtrate analyzed by GC. GC analysis shows 52% yield of 2,4-diethyl-oct-2-enal.

Example 42: Comparative Example

A 3 L three neck round bottom flask is charged with 20.8 g (708 mmol) of NaOH pellets. 75 mL of water is added and the mixture stirred by means of a magnetic stir bar until the NaOH is dissolved. 8.38 g (26 mmol) of tetrabutylammonium bromide is added. A 500 mL dropping funnel, glycol chilled condenser, and thermometer are attached to the round bottom. The entire apparatus is brought to 50° C. The dropping funnel is charged with a mixture of n-butyraldehyde (37.5 g, 520 mmol) and 2-ethylhexanal (133 g, 1040 mmol) and the aldehyde mixture is added slowly dropwise to the caustic mixture. After three hours, the mixture is cooled and poured into a 1 L separatory funnel. The bottom aqueous layer is separated. The upper organic phase is washed with water and brine. The organic layer is dried over $MgSO_4$, filtered, and the filtrate analyzed by GC. GC analysis shows 65% yield of 2,4-diethyl-oct-2-enal. GC analysis also shows the mixture contains 3.5% tributyl amine by weight.

Example 43: Comparative Example

Alkyldimethylbenzylammonium chloride is purchased from Sigma Aldrich as a semi-solid mixture of components where the alkyl chain can vary from C8 to C18. This material is heated to 65° C. in an oven to obtain a flowable composition. A 3 L three neck round bottom flask is charged with 20.8 g (708 mmol) of NaOH pellets. 75 mL of water is added and the mixture stirred by means of a magnetic stir bar until the NaOH is dissolved. 8.84 g of alkyldimethylbenzylammonium chloride (20-30 mmol) is added. A 500 mL dropping funnel, glycol chilled condenser, and thermometer are attached to the round bottom. The entire apparatus is brought to 50° C. The dropping funnel is charged with a mixture of n-butyraldehyde (37.5 g, 520 mmol) and 2-ethylhexanal (133 g, 1040 mmol) and the aldehyde mixture is added slowly dropwise to the caustic mixture. After three hours, the mixture is cooled and poured into a 1 L separatory funnel. The bottom aqueous layer is separated. The upper organic phase is washed with water and brine. The organic layer is dried over MgSO4, filtered, and the filtrate analyzed by GC. GC analysis shows 52% yield of 2,4-diethyl-oct-2-enal.

Example 44: Synthesis of Branched C12 Butyl Quat

To a 25 mL sealed flask was added 2,4-diethyl-N,N-dimethyloctan-1-amine (3.0 g, 14.06 mmol) and 1-bromobutane 1.51 mL, 14.06 mmol). The tube was sealed tightly using a Teflon screw cap and placed in a preheated oil bath at 120° C. A blast shield was placed in front of the reaction. The contents of the tube was stirred at 120° C. for 12 h. The reaction tube was removed from the oil bath and allowed to cool to room temperature. 1H-NMR of the crude reaction mixture shows complete conversion of C12-dimethyl amine to N-butyl-2,4-diethyl-N,N-dimethyloctan-1-aminium bromide (branched C12-butyl quat). The reaction mixture was diluted with water to make the final concentration to 75%.

1H NMR (500 MHz, CDC13)) δ3.75-3.47 (m, 6H), 3.47-3.32 (m, 12H), 3.17 (ddd, J=13.4, 9.2, 3.9 Hz, 2H), 1.91-1.62 (m, 6H), 1.52 (tq, J=7.1, 3.1 Hz, 4H), 1.48-1.07 (m, 28H), 1.05-0.73 (m, 29H) ppm. $^{13}$C NMR (126 MHz, CDC13) 568.84, 68.77, 64.45, 51.42, 51.07, 37.89, 37.86, 36.06, 35.94, 35.90, 32.85, 32.38, 31.69, 31.63, 28.78, 28.61, 25.99, 25.96, 25.77, 25.25, 24.86, 23.11, 23.07, 19.64, 14.15, 14.11, 13.76, 10.73, 10.67, 10.46, 10.01, 9.94 ppm

Example 45: Synthesis of C12-Enal Using N-butyl-2,4-diethyl-N,N-dimethyloctan-1-aminium Bromide (Branched C12-Butyl Quat.) as PTC To a 100 mL 3-neck flask equipped with a stir bar, reflux condenser, addition funnel and a temperature probe, NaOH (10.0 g, 125 mmol, 50% solution in wa), water (12.16 mL) and N-butyl-2,4-diethyl-N,N-dimethyloctan-1-aminium bromide (2.92 g, 6.25 mmol, 75% solution in water) prepared in the last step was added. The flask was placed in an oil bath and the contents were stirred at 50° C. A mixture of 2-ethyl hexaldehyde (24.37 mL, 156 mmol) and n-butyraldehyde (11.83 mL, 131 mmol) was charged in a separatory funnel and added to the stirred mixture dropwise. The addition was maintained at such a rate that the internal temperature of the reaction did not rise above 55° C. After the addition was complete, the heating was continued for overnight and the crude reaction mixture was analyzed by GC which showed 38.9% (area %) of C12-enal.

Example 46: Comparative Example

To a 100 mL 3-neck flask equipped with a stir bar, reflux condenser, addition funnel and a temperature probe, NaOH (10.0 g, 125 mmol, 50% solution in water), water (12.16 mL) and methyl-tributyl ammonium chloride (1.96 g, 6.25 mmol, 75% solution in water) was added. The flask was placed in an oil bath and the contents were stirred at 50° C. A mixture of 2-ethyl hexaldehyde (24.37 mL, 156 mmol) and n-butyraldehyde (11.83 mL, 131 mmol) was charged in a separatory funnel and added to the stirred mixture dropwise. The addition was maintained at such a rate that the internal temperature of the reaction did not rise above 55° C. After the addition was complete, the heating was continued for overnight and the crude reaction mixture was analyzed by GC which showed 44.7% (area %) of C12-enal.

In the specification, there have been disclosed certain embodiments of the invention and, although specific terms are employed, they are used in a generic and descriptive sense only and not for purposes of limitation, the scope of the invention being set forth in the following claims.

We claim:

1. A quaternary ammonium compound of the formula:

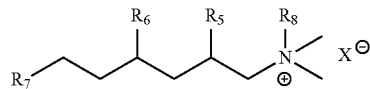

wherein R8 is methyl, ethyl, butyl, or benzyl, and X is a halide or alkosulfate,
wherein R5 and R6 are independently selected from the group consisting of $C_3H_7$, $C_2H_5$, and $CH_3$; and
wherein R7 is selected from the group consisting of $C_3H_7$, $C_2H_5$, $CH_3$ and H.

2. The quaternary ammonium compound of claim 1 wherein R6 is C2H5.

3. The quaternary ammonium compound of claim 1 wherein R5 and R6 independently are C2H5.

4. The quaternary ammonium compound of claim 1 wherein R5 is $CH_3$.

5. The quaternary ammonium compound of claim 4 wherein R5 is CH3 and R6 is C2H5.

6. The quaternary ammonium compound of claim 1 wherein R8 is benzyl or butyl.

7. The quaternary ammonium compound of claim 6 wherein X— is halide.

8. The quaternary ammonium compound of claim 6 selected from N-benzyl-2,4-diethyl-N,N-dimethyloctan-1-aminium chloride or N-butyl-2,4-diethyl-N,N-dimethyloctan-1-aminium bromide.

9. A composition comprising the quaternary ammonium compound of claim 1.

10. A composition comprising the quaternary ammonium compound of claim 9 wherein the composition does not contain combinations with other quaternary ammonium compounds.

11. The quaternary ammonium compound of claim 1 which is a disinfecting agent.

12. The quaternary ammonium compound of claim 11 having a minimum lethal concentration against at least one microbe selected from gram-positive bacteria, gram-negative bacteria, or yeast, when used at concentrations of less than 200 ppm.

13. The quaternary ammonium compound of claim 12 having a minimum lethal concentration against *E. coli, S. aureus* and *C-albicans* when used at concentrations of less than 200 ppm.

* * * * *